United States Patent [19]

Hamilton et al.

[11] Patent Number: 5,399,542
[45] Date of Patent: Mar. 21, 1995

[54] SUBSTITUTED BENZOXAZINONE CYCLOHEXANEDIONES AND THEIR HERBICIDAL USES

[75] Inventors: Christopher T. Hamilton, Indianapolis; Lowell D. Markley, Zionsville; Todd C. Geselius, Indianapolis, all of Ind.

[73] Assignee: DowElanco, Indianapolis, Ind.

[21] Appl. No.: 170,105

[22] Filed: Dec. 20, 1993

[51] Int. Cl.$^6$ .................. A01N 43/84; C07D 265/36
[52] U.S. Cl. .................. 504/224; 504/225; 544/105
[58] Field of Search ............... 544/105; 504/224, 225

[56] References Cited

U.S. PATENT DOCUMENTS

| | | | |
|---|---|---|---|
| 4,631,081 | 12/1986 | Watson et al. | 71/94 |
| 4,680,400 | 7/1987 | Bird et al. | 546/141 |
| 4,692,553 | 9/1987 | Keil et al. | 564/185 |
| 4,983,211 | 1/1991 | Markley et al. | 71/94 |
| 5,007,952 | 4/1991 | Kume et al. | 71/73 |
| 5,141,551 | 8/1992 | Kawaguchi et al. | 504/225 |

OTHER PUBLICATIONS

D. R. Shridhar et al., Organic Preparations And Procedures Int., "Synthesis of 2H-1-4-Benzoxazin-3(4H)-Ones", 14(3), pp. 195-224 (1982).

Xian Huang et al., Synthesis, "Synthesis of 3-Oxo-3,-4-dihydro-2H-1,4-benzoxazines and -1,4-Benzothiazines under Phase-Transfer Catalysis", pp. 851-853 (1984).

*Primary Examiner*—Glennon H. Hollrah
*Assistant Examiner*—S. Mark Clardy
*Attorney, Agent, or Firm*—S. Preston Jones; D. Wendell Osborne

[57] ABSTRACT

The present disclosure is directed to substituted cyclohexanedione compounds, the preparation of said compounds, compositions containing said compounds and the use of said compositions in the selective pre- and postemergent kill and control of grassy weeds in the presence of various broad-leafed and grassy crop plants.

24 Claims, No Drawings

SUBSTITUTED BENZOXAZINONE CYCLOHEXANEDIONES AND THEIR HERBICIDAL USES

FIELD OF THE INVENTION

The present invention is directed to substituted benzoxazinone cyclohexanedione compounds, compositions containing said compounds and the use of said compositions in the selective pre- and postemergent kill and control of grassy weeds growing in broadleaf and some grassy crops.

SUMMARY OF THE INVENTION

The present invention is directed to cyclohexanedione compounds corresponding to the formula

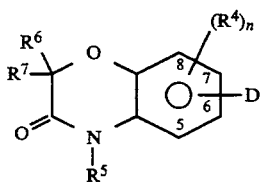

I

Wherein in this and in subsequent formula depictions,

D is attached in the 6 or 7 ring position and represents the radical

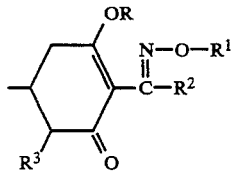

R represents —H, or acyl;

$R^1$ represents $C_1$–$C_3$ alkyl, $C_3$–$C_5$ alkenyl or $C_3$–$C_5$ haloalkenyl, arylalkenyl wherein aryl represents phenyl or pyridinyl substituted with from 0 to 4 halo or —$CF_3$ groups or mixtures thereof and alkenyl contains from $C_3$–$C_5$ carbon atoms;

$R^2$ represents $C_1$–$C_3$ alkyl;

$R^3$ represents —H or —$CH_3$;

$R^4$ each independently represents —H, halo, $C_1$–$C_4$ alkyl or $C_1$–$C_4$ alkoxy;

$R^5$ represents —H, $C_1$–$C_4$ alkyl, $C_1$–$C_4$ haloalkyl, $C_3$–$C_5$ alkenyl, $C_3$–$C_5$ haloalkenyl, $C_3$–$C_5$ alkynyl, $C_3$–$C_5$ haloalkynyl, alkoxyalkyl wherein the alkoxy and alkyl group each contains from $C_1$–$C_4$ carbon atoms or alkylthioalkyl wherein each alkyl group thereof contains from $C_1$–$C_4$ carbon atoms;

$R^6$ represents $R^5$, $C_1$–$C_4$ alkoxy or aryl wherein aryl is phenyl or pyridinyl substituted with from 0–3 halogen or methyl groups.

$R^7$ represents —H or $C_1$–$C_4$ alkyl; and n represents the integer 1, 2 or 3;

and the herbicidally acceptable organic and inorganic salts thereof.

In addition, the present invention is directed to compositions containing the compounds of Formula I, as an active ingredient therein, and to methods of using said compositions in the selective pre- and postemergent kill and control of grassy weeds, especially in the presence of crop plants such as those hereinafter set forth. The present invention is also directed to a method of preparing the compounds of Formula I.

In the present specification and claims, the herbicidally acceptable organic and inorganic salts of Formula I, which are useful in the selective pre- and postemergent kill and control of grassy weeds, are those conventionally employed and include the alkali metal salts of the metals sodium, potassium, rubidium, lithium, cesium and the like; alkaline earth metal salts of the metals calcium, strontium, magnesium, barium and the like; salts of the metals manganese, copper and iron; and ammonium and phosphonium salts such as the mono-, di-, tri- and tetraalkylammonium salts; triphenylphosphonium salts and the like.

In the present specification and claims, the term "halo", as used alone or as a substituent, designates the halogens bromo, chloro, fluoro and iodo.

In the present specification and claims, the term "alkyl" designates alkyl groups having carbon chain lengths of 1 to 3 or 1 to 4 carbon atoms and may be straight or branched chain as appropriate within the chain length such as, for example, methyl, ethyl, n-propyl, i-propyl, n-butyl, i-butyl, sec.-butyl or t-butyl.

In the present specification and claims, the term "$C_1$–$C_4$ alkoxy" designates straight or branched chain alkoxy groups of 1 to 4 carbon atoms such as, for example, methoxy, ethoxy, n-propoxy, i-propoxy, n-butoxy, i-butoxy, sec-butoxy or t-butoxy.

In the present specification and claims, the term "$C_1$–$C_4$ haloalkyl" designates straight or branched chain alkyl groups of 1 to 4 carbon atoms substituted with from 1 halo atom up to perhalo substitution.

In the present specification and claims, the terms "$C_3$–$C_5$ alkenyl" designates straight or branched chain alkenyl groups of 3 to 5 carbon atoms, such as, for example, allyl, 2-butenyl, 3-butenyl, methallyl or pentenyl.

In the present specification and claims, the term "$C_3$–$C_5$ haloalkenyl" designates straight or branched chain alkenyl groups of 3 to 5 carbon atoms, substituted with from 1 halo atom up to perhalo substitution, such as, for example, 3-chloro-2-propenyl, 3,3,2-trifluoropropenyl and the like.

In the present specification and claims, the term "$C_3$–$C_5$ alkynyl" designates straight or branched chain alkynyl groups of 3 to 5 carbon atoms including, for example, propargyl, 2-butynyl or 3-butynyl.

In the present specification and claims, the term "$C_3$–$C_5$ haloalkynyl" designates straight or branched chain alkynyl groups of 3 to 5 carbon atoms substituted with from 1 halo atom up to perhalo substitution.

In the present specification and claims, the term "acyl" designates radicals of the formula $R^8$—C(O)— wherein $R^8$ represents $C_1$–$C_4$ alkyl, $C_1$–$C_4$ haloalkyl or phenyl.

The active ingredients of Formula I wherein R represents hydrogen constitutes a preferred embodiment. The active ingredients of Formula I wherein $R^1$ and $R^2$ each represent alkyl constitute a more preferred embodiment.

In the present invention, it is to be noted that all substituent groups are sterically compatible with each other. The term "sterically compatible" is employed to designate substituent groups which are not affected by steric hindrance as this term is defined in "The Condensed Chemical Dictionary", 7th edition, Reinhold Publishing Co., N.Y. page 893 (1966) which definition is as follows:

"steric hindrance. A characteristic of molecular structure in which the molecules have a spatial arrangement of their atoms such that a given reaction with another molecule is prevented or retarded in rate."

Sterically compatible may be further defined as reacting compounds having substituents whose physical bulk does not require confinement within volumes insufficient for the exercise of their normal behavior as discussed in *Organic Chemistry* by D. J. Cram and G. Hammond, 2nd edition, McGraw-Hill Book Company, N.Y., page 215 (1964).

The cyclohexanediones of the present invention which correspond to Formula I, may exist in either form or in admixtures of the isomeric forms representing D as set forth below in Formulae Ia and Ib:

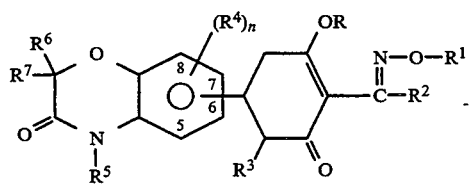

or

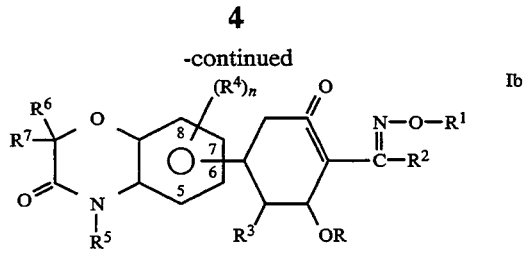

The cyclohexanediones of the present invention, when R is hydrogen, can exist in any of the four tautomeric forms set forth hereinbelow:

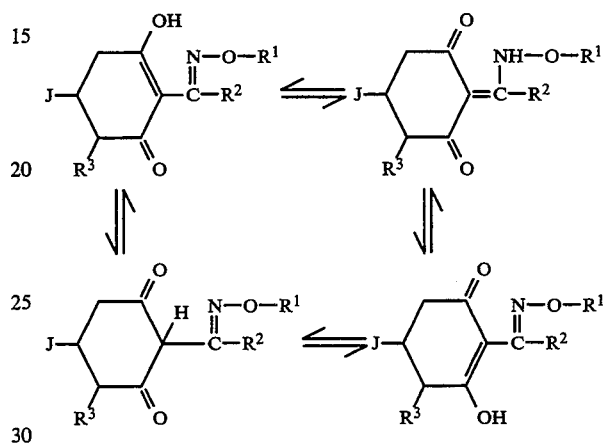

The compounds of the present invention are generally low melting crystalline solids at ambient temperatures which are soluble in many organic solvents.

Representative compounds which correspond to Formula I (Compounds of Formulae II and III) include the compounds set forth below in Tables I and II.

TABLE I

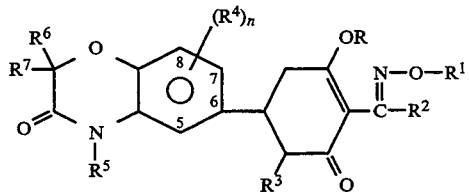

| R | $R^1$ | $R^2$ | $R^3$ | $(R^4)_n$ | $R^5$ | $R^6$ | $R^7$ |
|---|---|---|---|---|---|---|---|
| —H | —Et | —Et | —H | —H | —H | —H | —H |
| —H | —Et | -n-Pr | —H | —H | —H | —Me | —H |
| —H | —Et | —Et | —H | —H | —H | —Me | —Me |
| —H | —Et | -n-Pr | —H | —H | —Me | —Me | —Me |
| —H | —CH$_2$—CH=CH$_2$ | —Et | —H | 7-Cl | —H | —H | —H |
| —H | —Et | —Et | —Me | —H | —H | —H | —H |
| —H | —Et | —Et | —H | —H | —CH$_2$—CH=CH$_2$ | —Me | —H |
| —H | —CH$_2$—CH=CHCl | -n-Pr | —H | —H | —H | —Me | —Me |
| —H | —Et | —Et | —H | —H | —H | —CH$_2$OEt | —H |
| —H | —Et | —Et | —H | —H | —H | $R^6 + R^7=$ | =C(CH$_3$)$_2$ |
| —H | —CH$_2$—CH=CH$_2$ | —Et | —H | —H | —H | —Ph | —H |
| —H | —Et | —Et | —Me | —H | —Me | —Me | —H |
| —H | —Et | —Et | —H | 8-Cl | —H | —Me | —Me |
| —H | —Et | —Et | —H | —H | —CH$_2$—C≡CH | —H | —H |
| —H | —Et | —Et | —H | —H | —H | —CH(CH$_3$)$_2$ | —H |
| —H | —Et | —Et | —H | —H | —H | —Et | —Me |
| —C(O)CH$_3$ | —Et | —Et | —H | —H | —H | —Me | —H |
| —H | —Et | -n-Pr | —H | 7-CH$_3$ | —H | —H | —H |
| —H | —Et | -n-Pr | —H | 7-CH$_3$ | —H | —Me | —H |
| —H | —Et | —Et | —H | —H | —H | -n-Pr | —H |
| —H | —Et | —Et | —H | —H | —H | -n-Pr | —Me |
| —H | —Et | —Et | —H | —H | —CH$_2$OMe | —H | —H |
| —H | —Et | —Et | —H | —H | —CH$_2$CH$_2$Cl | —Me | —H |
| —H | —Et | -n-Pr | —H | —H | —CH(CH$_3$)$_2$ | —H | —H |
| —H | —Et | -n-Pr | —Me | —H | —Me | —H | —H |

TABLE I-continued

II

| R | R¹ | R² | R³ | (R⁴)ₙ | R⁵ | R⁶ | R⁷ |
|---|---|---|---|---|---|---|---|
| —H | —CH₂CH=CH₂ | —Et | —H | 5,7-diMe | —H | —H | —H |
| —H | —CH₂CH=CHPh | —Et | —H | —H | —H | —Me | —H |
| —H | —Et | —Et | —H | —H | —H | —Ph | —Me |
| —Na | —Et | —Et | —H | —H | —H | —Me | —Me |
| —H | —Et | —Et | —H | —H | —CH₂Ph | —H | —H |
| —H | —Et | —Et | —H | —H | —(CH₂)₃Cl | —H | —H |
| —H | —Et | —Et | —H | 8-F | —H | —Me | —Me |
| —H | —Et | —Et | —H | 5-F | —H | —Me | —Me |
| —H | —Et | -n-Pr | —H | —H | —Et | —Me | —H |
| —H | —Et | —Et | —H | —H | -n-Pr | —H | —CH₂CH=CH₂ |
| —H | -i-Pr | —Et | —Me | —H | —H | —CH₂CH=CH₂ | —H |
| —H | —Et | —Et | —Me | —H | —CH₂CH₂S—Et | —CF₃ | —H |
| —H | —Et | —Et | —H | —H | —CH₂O-t-Bu | —CH₂CH=CH₂ | -n-Pr |
| —H | —Et | —Me | —H | —H | —CH₂CH=CHCF₃ | —F | —H |
| —H | —Et | —Me | —Me | —H | —CH(Cl)C≡CH | —H | -i-Pr |
| —H | —Et | -i-Pr | —H | 5-OCH₃ | —CH₂CH=CH₂ | 2-(3-F,5-—CF₃)—Py | —H |
| —K | —CH₂—CH=CH—(2-Cl,5-CF₃—Ph) | -i-Pr | —H | —H | —H | —H | —H |

TABLE II

III

| R | R¹ | R² | R³ | (R⁴)ₙ | R⁵ | R⁶ | R⁷ |
|---|---|---|---|---|---|---|---|
| —H | —Et | —Et | —H | —H | —H | —H | —H |
| —H | —Et | -n-Pr | —H | —H | —H | —Me | —H |
| —H | —Et | —Et | —H | —H | —H | —Me | —Me |
| —H | —Et | -n-Pr | —H | —H | —Me | —Me | —Me |
| —H | —CH₂—CH=CH₂ | —Et | —H | 6-Cl | —H | —H | —H |
| —H | —Et | —Et | —Me | —H | —H | —H | —H |
| —H | —Et | —Et | —H | —H | —CH₂—CH=CH₂ | —Me | —H |
| —H | —CH₂—CH=CHCl | -n-Pr | —H | —H | —H | —CH₂OEt | —H |
| —H | —Et | —Et | —H | —H | —H | R⁶ + R⁷= | =C(CH₃)₂ |
| —H | —CH₂—CH=CH₂ | —Et | —H | —H | —H | —Ph | —H |
| —H | —Et | —Et | —Me | —H | —Me | —Me | —H |
| —H | —Et | —Et | —H | 8-Cl | —H | —Me | —Me |
| —H | —Et | —Et | —H | —H | —CH₂—C≡CH | —H | —H |
| —H | —Et | —Et | —H | —H | —H | —CH(CH₃)₂ | —H |
| —H | —Et | —Et | —H | —H | —H | —Et | —Me |
| —C(O)CH₃ | —Et | —Et | —H | —H | —H | —Me | —H |
| —H | —Et | -n-Pr | —H | 6-CH₃ | —H | —H | —H |
| —H | —Et | -n-Pr | —H | 6-CH₃ | —H | —Me | —H |
| —H | —Et | —Et | —H | —H | —H | -n-Pr | —H |
| —H | —Et | —Et | —H | —H | —H | -n-Pr | —Me |
| —H | —Et | —Et | —H | —H | —CH₂OMe | —H | —H |
| —H | —Et | —Et | —H | —H | —CH₂CH₂Cl | —Me | —H |
| —H | —Et | -n-Pr | —H | —H | —CH(CH₃)₂ | —H | —H |
| —H | —Et | -n-Pr | —Me | —H | —Me | —H | —H |
| —H | —CH₂CH=CH₂ | —Et | —H | 6,8-diMe | —H | —H | —H |
| —H | —CH₂CH=CHPh | —Et | —H | —H | —H | —Me | —H |
| —H | —Et | —Et | —H | —H | —H | —Ph | —Me |
| —Na | —Et | —Et | —H | —H | —H | —Me | —Me |
| —H | —Et | —Et | —H | —H | —CH₂Ph | —H | —H |
| —H | —Et | —Et | —H | —H | —(CH₂)₃Cl | —H | —H |
| —H | —Et | —Et | —H | 8-F | —H | —Me | —Me |
| —H | —Et | —Et | —H | 5-F | —H | —Me | —Me |
| —H | —Et | -n-Pr | —H | —H | —Et | —Me | —H |
| —H | —Et | —Et | —H | —H | -n-Pr | —H | —H |
| —H | -i-Pr | —Et | —Me | —H | —H | —CH₂CH=CH₂ | —H |

TABLE II-continued

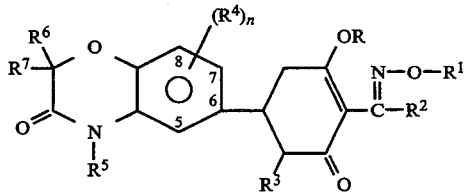

III

| R | R¹ | R² | R³ | (R⁴)$_n$ | R⁵ | R⁶ | R⁷ |
|---|----|----|----|----------|-----|-----|-----|
| —H | —Et | —Et | —Me | —H | —CH$_2$CH$_2$S—Et | —CF$_3$ | —H |
| —H | —Et | —Et | —H | —H | —CH$_2$O-t-Bu | —CH$_2$CH=CH$_2$ | -n-Pr |
| —H | —Et | —Me | —H | —H | —CH$_2$CH=CHCF$_3$ | —F | —H |
| —H | —Et | —Me | —Me | —H | —CH(Cl)C≡CH | —H | -i-Pr |
| —H | —Et | -i-Pr | —H | 5-OCH$_3$ | —CH$_2$CH=CH$_2$ | 2-(3-F,5-—CF$_3$)—Py | —H |
| —K | —CH$_2$—CH=CH—(2-Cl,5-CF$_3$—Ph) | -i-Pr | —H | —H | —H | —H | —H |

The following examples illustrate the present invention and the manner by which it can be practiced but, as such, should not be construed as limitations upon the overall scope of the same.

In the preparation of the compounds of the present invention, the amounts of the reactants to be employed are not critical. In most cases it is preferred to employ substantially equimolar amounts of the reactants. Depending upon the specific type of reaction taking place, it may be beneficial that a given one of the reactants be present in a slight excess to obtain the highest yields of the desired product.

Since the hereinabove and hereinafter set forth compound preparation procedures employ only standard chemistry practices and it is known that slightly different reactants can require slightly different reaction parameters, it is to be understood that minor modifications to the reaction parameters set forth such as the use of an equivalent solvent, the use of an excess of one of the reactants, the use of a catalyst, the use of higher or lower temperatures and/or pressure equipment, high speed mixing and other such conventional changes are within the scope of this invention.

The desired product can be separated from the reaction product of the above preparative procedures employing conventional separatory procedures known to those skilled in the art including steps such as, for example, solvent extraction, filtration, water washing, column chromatography, neutralization, acidification, crystallization and distillation.

The compounds corresponding to Formula I of the present invention, wherein R and R⁵ are both hydrogen, can be prepared by the reaction of an appropriate ketone reactant, corresponding to Formula IV:

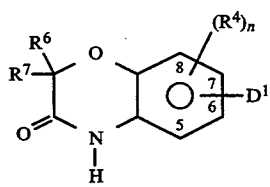

IV wherein R², R³, R⁴, R⁶, R⁷, and n are hereinbefore defined and D¹ represents the radical

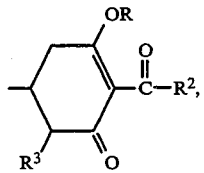

with an excess of an appropriate alkoxyamine reactant corresponding to the formula R¹ONH$_2$ (wherein R¹ is as hereinbefore defined) or an inorganic salt thereof and from about 1–2 moles of a base. This reaction can be conducted at temperatures of from about 0° to about 100° C. in the presence of a solvent.

Representative solvents include, for example, dimethyl sulfoxide, C$_1$–C$_4$ alkanols, hydrocarbons, cyclic ethers, halohydrocarbons, and the like, with the C$_1$–C$_4$ alkanols being preferred.

Representative bases include, for example, the carbonates, acetates, alcoholates and hydroxides of the alkali and alkaline earth metals, in particular, sodium and potassium, and organic bases, such as pyridine or tertiary amines, with anhydrous sodium acetate being preferred.

The reaction time can extend for a time of from a few minutes up to 24 hours or more, depending upon the specific reactants and reaction temperature. The product can be recovered employing one or more of the conventional separatory techniques set forth hereinabove.

The herbicidally acceptable organic and inorganic salts of the compounds of Formula I can be prepared from said compounds of Formula I employing conventional procedures. The salts are conveniently obtained by mixing an appropriate organic or inorganic base with a compound of Formula I where R is hydrogen, if necessary, in an inert solvent; distilling off the solvent and recrystallizing the residue as necessary.

Representative solvents include, for example, water, C$_1$–C$_4$ alkanols, hydrocarbons, cyclic ethers, halohydrocarbons, and the like, with the C$_1$–C$_4$ alkanols being preferred.

Representative bases include, for example, the carbonates, alcoholates and hydroxides of the alkali and alkaline earth metals, in particular, sodium and potassium, and organic bases, such as pyridine or tertiary amines. For ease of formulation, these salts are prepared by neutralization of the above compound of Formula I in an equimolar amount of the base. Other metal salts such as, for example, the manganese, copper, zinc and iron salts can be prepared from the alkali metal salts employing conventional salt forming procedures for these metals. In addition, the ammonium and phosphonium salts can be prepared employing conventional ammonium and phosphonium salt forming procedures.

The compounds corresponding to Formula I, wherein R is acyl can be prepared by reacting a compound of Formula I, wherein R is hydrogen with a compound of the formula acyl-L wherein L is a leaving group such as, for example, chloride, bromide, iodide, nitrate, sulfate, methyl sulfate, ethyl sulfate, tetrafluoroborate, hexafluorophosphate, methanesulfonate, fluorosulfonate and trifluoromethanesulfonate. This reaction can be carried out employing the appropriate conventional reaction procedures such as taught in U.S. Pat. Nos. 4,631,081 and 4,680,400.

The compounds corresponding to Formula IV wherein $R^5$ is other than hydrogen and which corresponds to Formula IVb

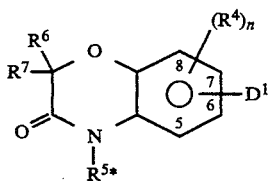

IVb can be prepared by the reaction of a compound which corresponds to Formula IVa

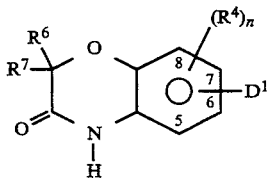

IVa with a compound of the formula $R^{5*}$-X wherein $R^{5*}$ represents $R^5$ less hydrogen and X is a leaving group such as, for example, chloride, bromide, iodide or sulfonate. The reaction is conducted in the presence of from about 1 to about 3 equivalents of a suitable base such as, for example, sodium hydride or potassium carbonate and a polar solvent such as, for example, dimethyl formamide or methyl sulfoxide. The reaction is usually carried out at a temperature of from about 0° to about 140° C. for reaction times of from about 0.5 to about 24 hours, depending on the specific $R^{5*}$-X reactant.

The compounds corresponding to Formula IVa wherein $R^5$ and $R^7$ are both hydrogen can be prepared by the reaction of an appropriate reactant corresponding to Formula V

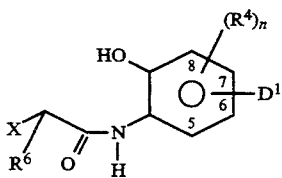

V with from about 2 to about 4 equivalents of a suitable base such as, for example, sodium bicarbonate in water at a temperature of from about 20° to about 100° C. or with from about 2 to about 4 equivalents of a sodium ethoxide (prepared by dissolving sodium metal in absolute ethanol) at a temperature of from about 20° C. to the reflux temperature. The reaction is usually carried out in the presence of a suitable solvent such as, for example, water, lower alkanol, dimethyl formamide or methyl sulfoxide. The reaction mixture is diluted with water, acidified to a pH of about 2–4 with 1N HCl and the product recovered by conventional techniques such as filtration or extraction.

The compounds corresponding to Formula IVa wherein $R^6$ is alkoxymethyl can also be prepared by the reaction of an appropriate reactant corresponding to Formula Va

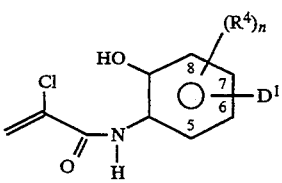

Va with excess sodium alkoxide(prepared by dissolving sodium metal in the alkanol corresponding to the desired alkoxy group of $R^6$) at a temperature of from about 20° C. up to the reflux temperature for a period of from 0.5 to 4.0 hours. The reaction is carried out in the presence of the same alcohol solvent used to prepare the alkoxide. The reaction mixture is diluted with water, acidified to a pH of about 2–4 with 1N HCl and the product recovered by conventional techniques such as filtration or extraction.

The compounds corresponding to Formula Va can be prepared by the treatment of a compound corresponding to Formula VI

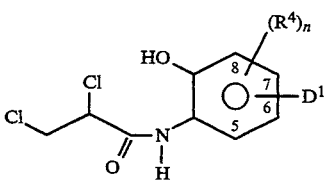

VI with from about 1 to about 10 equivalents of a base such as, for example, triethylamine or pyridine in a solvent such as, for example, acetonitrile or tetrahydrofuran at temperatures of from 20° C. up to the reflux temperature for a period of from 0.5 to 24.0 hours. The product is recovered by conventional techniques such as filtration or extraction.

The compounds corresponding to Formula V can be prepared by the treatment of a compound corresponding to Formula VII

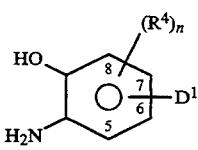

VII with a compound of the formula

Y—C(O)—CH(X)—$R^6$ wherein X and $R^6$ are as defined hereinabove and Y is a leaving group such as, for example, chloride, bromide or —O—C(=O)—R. The reaction is generally carried out at temperatures of from 0° to about 40° C. in the presence of from about 2 to about 4 equivalents of anhydrous sodium acetate, or other suitable base, such as pyridine, in a solvent such as tetrahydrofuran for a period of from about 1 to about 12 hours. The reaction mixture is diluted with water, acidified to a pH of about 2–4 with 1N HCl and the product recovered by conventional techniques such as filtration or extraction.

The compounds corresponding to Formula VI can be prepared by the treatment of a compound corresponding to Formula VII with a compound of the formula Cl—C(O)—CH(Cl)—CH$_2$—Cl The reaction is generally carried out at temperatures of from 0° to about 40° C. in the presence of from about 2 to about 4 equivalents of anhydrous sodium acetate in a solvent such as tetrahydrofuran for a period of from about 1 to about 12 hours. The reaction mixture is diluted with water, acidified to a pH of about 2–4 with 1N HCl and the product recovered by conventional techniques such as filtration or extraction.

In another procedure of converting the compounds of Formula VII to the compounds of Formula V and the subsequent conversion of the compounds of Formula V to the Compounds of Formula IVb can be accomplished in a single operation following the method reported by Shridhar in *Org Prep Proceed Int'l*, 1982, 14(3), page 195; with the modification of adding an additional equivalent of sodium bicarbonate.

The compounds of Formula VII are usually not isolated, but are normally employed as a concentrated solution in an inert organic solvent after preparation from compounds of Formula VIII

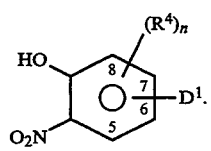
VIII

The reaction can be accomplished by hydrogenation under a 10 to 50 lbs pressurized hydrogen atmosphere in the presence of a catalyst such as platinum or palladium, with a sulfided 5 percent platinum on carbon being preferred, and in the presence of an aprotic solvent such as ethyl acetate, tetrahydrofuran or dioxane with ethyl acetate being preferred. The reaction requires from about 1 to about 6 hours at temperatures of from about 15° to about 30° C. When the reaction is complete, the excess hydrogen is removed by sparging with nitrogen gas, the catalyst is then removed by filtration through an absorbent such as diatomaceous earth, silica gel and the like and the filtrate solution is evaporated under reduced pressure until the desired compound of Formula VII is in a concentration of around 50 percent in the remaining solvent. The viscous oily product which remains is then employed directly in the next reaction as described hereinabove.

The compounds corresponding to Formula VII can also be prepared in a two step procedure wherein an appropriate reactant corresponding to Formula VIII dissolved in ethyl acetate is treated in a pressurizable reactor with a platinum or palladium on carbon catalyst and agitated while pressurizing the reactor with hydrogen for a period of from one to 24 hours. The mixture is then sparged with nitrogen gas to remove residual hydrogen and filtered through an absorbent such as diatomaceous earth, silica gel and the like. The solvent is removed by evaporation and the residue dissolved in tetrahydrofuran or dioxane. The solution is cooled to a temperature of from about 0° to about 10° C. and treated with anhydrous sodium acetate and then with chloroacetyl chloride. The mixture is allowed to come to room temperature and diluted with cold dilute HCl. The product can be recovered by filtration or other conventional solid-liquid separatory procedures.

The compounds corresponding to Formula VIII

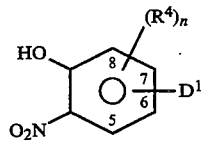
VIII can be prepared by nitration with 1 to 2 equivalents of concentrated nitric acid (90 percent nitric acid) of a compound corresponding to Formula IX

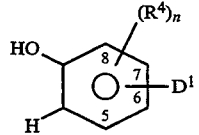
IX in a solvent such as dichloromethane, 1,2-dichloroethane or acetic anhydride at a temperature of from about 0° to about 5° C. After about 0.5 to about 2.0 hours, the reaction mixture is partitioned between water and dichloromethane. The product is contained in the organic layer and is recovered by conventional separatory procedures such as drying and evaporation. The product can be further purified, if desired, by conventional recrystallization techniques.

The compounds corresponding to Formula VIIIa

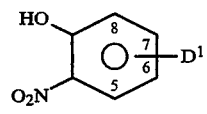
VIIIa and their preparation is taught in U.S. Pat. No. 4,692,553.

The compounds corresponding to Formula X and their preparation is taught in U.S. Pat. No. 4,983,211.

The compounds corresponding to Formula IV can also be prepared in a two step procedure wherein an appropriate reactant corresponding to Formula X

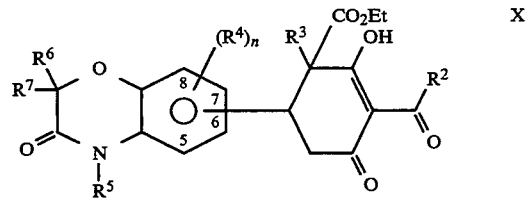
X wherein $R^2$, $R^3$, $R^4$, $R^5$, $R^6$, $R^7$, and n are hereinbefore defined is first reacted with 2 to 4 equivalents of a 1 to 2N concentration of an alkaline base, preferably 1N sodium hydroxide in water at a temperature of between about 40° and about 100° C. for a period of from about 2 to about 48 hours. The reaction mixture is then cooled to between about 20° and about 40° C. and acidified with excess (4 to 10 equivalents) of 1N to concentrated hydrochloric acid to obtain an acidic aqueous solution or a suspension of an intermediate compound of the formula

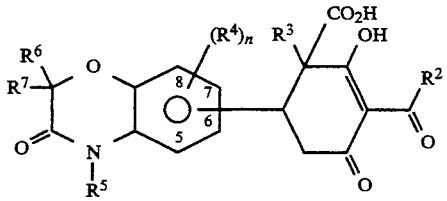

XI which often spontaneously decarboxylates to the desired product of Formula IV upon standing for from 1 to about 72 hours. Alternatively, the compound of Formula XI can be isolated by conventional techniques such as filtration or extraction and then heated at a temperature of from about 80° to about 140° C. in the presence of a solvent such as methyl sulfoxide or sulfolane for a period of from about 0.2 to about 0.5 hours to effect conversion of the compound to the compound of Formula IV. The product can be recovered by diluting the reaction mixture with water and removing the product therefrom by conventional techniques such as filtration or extraction.

The compounds corresponding to Formula XI can be prepared by heating a compound corresponding to Formula XII

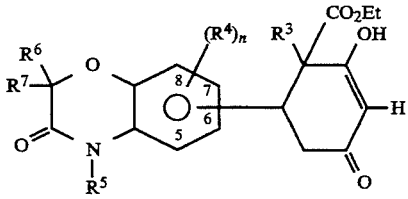

XII in a solvent such as, for example, chloroform or benzene that contains from 1–2 equivalents of an appropriate alkanoic anhydride and 1–2 equivalents of a base such as, for example, 4-dimethylaminopyridine or imidazole, at a temperature of from about 40° C. up to the reflux temperature of the mixture. After a heating period of from about 4 to about 24 hours, the reaction mixture is cooled to room temperature, washed with 1N HCl and then with a saturated NaCl solution, dried and the solvent removed under reduced pressure. The product is then purified using conventional techniques such as filtration or extraction. The compounds of Formula XI normally exist as mixtures of diastereomers in variable relative composition.

The compounds corresponding to Formula XII can be prepared by the reaction of an appropriate reactant corresponding to Formula XIII

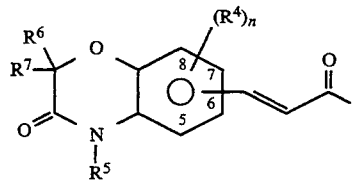

XIII wherein $R^4$, $R^5$, $R^6$, $R^7$, and n are hereinbefore defined, in an alkanol solvent with a solution prepared by mixing equimolar amounts of a solution of diethyl malonate (or mono alkyl substituted derivative thereof) in a $C_1$–$C_4$ alkanol and a fresh solution of sodium metal dissolved in a $C_1$–$C_4$ alkanol. The mixture is stirred at a temperature of from about 20° C. up to the reflux temperature of the mixture for a period of about 2 to about 24 hours. The reaction mixture is cooled to room temperature, diluted with water, acidified to a pH of about 2–4 with 1N hydrochloric acid and the product is recovered by conventional techniques such as filtration or extraction. The compounds of Formula XII normally exist as mixtures of diastereomers in variable relative composition.

The compounds corresponding to Formula XIII can be prepared by the reaction of an appropriate reactant corresponding to Formula XIV

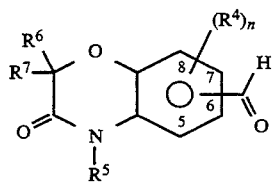

XIV wherein $R^4$, $R^5$, $R^6$, $R^7$ and n are hereinbefore defined with acetone in water and from about 0.1 to about 2 equivalents of a base such as, for example, sodium hydroxide. The reaction is conducted at from about 20° C. up to the reflux temperature of the mixture for a period of about 0.5 to about 48 hours. The reaction mixture is diluted with water, acidified to a pH of about 2–4 with 1N hydrochloric acid and the product is recovered by conventional techniques such as filtration or extraction. Alternatively, the reaction can be performed with an acetone derivative such as 1-triphenylphosphoranylidene-2-propanone in an inert solvent such as benzene, toluene or chloroform.

The compounds corresponding to Formula XIV wherein the aldehyde group is attached to the 6 ring position and corresponding to Formula XIVa

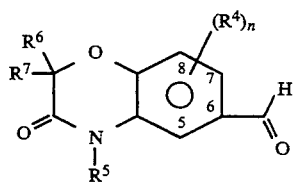

XIVa wherein $R^4$, $R^5$, $R^6$, $R^7$, and n are hereinbefore defined can be prepared by formylation of a compound of Formula XV,

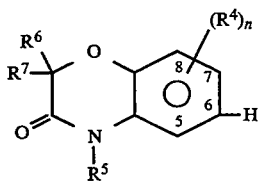

for example, by treatment of said compound with a 5 to 10 equivalent excess of α,α-dichloromethyl ether in the presence of a 2 to 3 equivalent excess of titanium (IV) chloride in a solvent such as, for example, dichloromethane or 1,2-dichloroethane at room temperature.

The compounds corresponding to Formula XV can be prepared from the appropriately substituted 2-aminophenol of Formula XVI

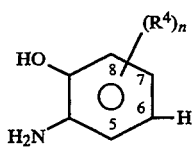

according to the known methods taught by Shridhar, *Org Prep Proceed Int'l*, 1982, 14(3), 195 or Huang, *Synthesis*, 1984, page 851.

The compounds corresponding to Formula XIV wherein the aldehyde group is attached to the 7 ring position and corresponding to Formula XIVb

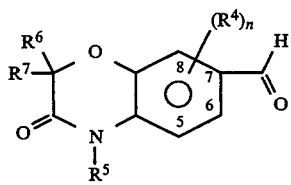

wherein $R^4$, $R^5$, $R^6$, $R^7$, and n are hereinbefore defined can be prepared via an appropriate aminophenol derivative of Formula XVII

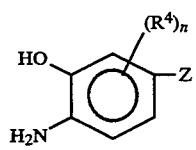

wherein $R^4$ and n are as defined hereinabove and Z represents a carboxaldehyde, a protected carboxaldehyde (for example, ethylenedioxy acetal) or a carboxaldehyde precursor (for example, carbinol). The reactant can be converted to the benzoxazine compound of Formula XVIII

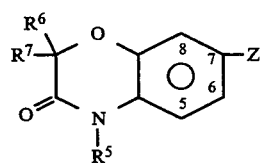

via the previously outlined procedures set forth for converting the compound of Formula XVI to the compound of Formula XV and followed by the procedures set forth for converting the compound of Formula VII through the various intermediates to the compound of Formula IVb. The thus prepared compound of Formula XVIII is then subjected to a deprotection procedure or other conventional procedures to convert the Z group to a carboxaldehyde to produce compounds corresponding to Formula XIVb.

In the compound preparation procedures set forth hereinabove where no specific substituent is set forth for the $R^5$ grouping, the $R^5$ substituent is assumed to be hydrogen. The hydrogen substituent can be converted to the other listed $R^5$ substituents via the procedure set forth for the transformation of the compound of Formula IVa to the compound of Formula IV.

The following Examples illustrate the present invention and the manner by which it can be practiced, but as such, should not be construed as limitations upon the overall scope of the same.

EXAMPLE I 2-(1-(Ethoxyimino)propyl)-3-hydroxy-5-(3-oxo-(2H,4H)-1,4-benzoxazin-6-yl)cyclohex-2-en-1-one

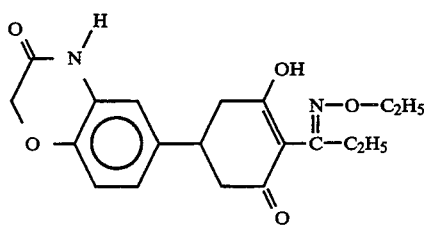

A solution of 1.4 grams(g) (4.4 mmol) of 2-propionyl-3-hydroxy-5-(3-oxo-(2H, 4H)-1,4-benzoxazin-6-yl)cyclohex-2-en-1-one in 40 milliliters (mL) of methyl sulfoxide was mixed with 0.50 g (5.2 mmol) of ethoxyamine hydrochloride and 0.40 g (4.9 mmol) of anhydrous sodium acetate. The resulting clear amber solution was stirred at ambient temperature under a nitrogen atmosphere for 4 hours. The mixture was diluted with 300 mL of water and extracted thrice with 20 mL portions of dichloromethaneo The extracts were combined, washed with aqueous sodium chloride, dried over $MgSO_4$ and filtered. The solution was then eluted through a short column of silica gel and flushed with 100 mL of dichloromethane. Evaporation of the solvent gave the crude product as a yellow solid which was triturated in warm ether and filtered to afford the purified above-named product, as a light yellow solid, in a yield of 1.1 g (69 percent of theoretical). The title compound melted at 171°-172° C., with decomposition; $^1$H NMR:(3:1 $CDCl_3$-DMSO-$d_6$) d1.09 (t, J=7 Hz,3H, —$CCH_2CH_3$), 1.28 (t, J=7 Hz, 3H, —$OCH_2CH_3$) 2.56–3.51 (m, 7H), 4.18(q, J=7 Hz, 2H,—$OCH_2CH_3$), 4.48 (s,2H, —$OCH_2C$=O), 6.85 (s, 3H, aromatic H's), 10.41 (broad s, 1H, —N—H), enol O—H not observed; (Compound 1).

| Analysis: | percent | | |
|---|---|---|---|
| | C | H | N |
| Calc. for $C_{19}H_{22}N_2O_5 \cdot 0.2$ $H_2O$: | 63.04 | 6.24 | 7.74 |
| Found: | 63.08 | 6.18 | 7.64 |

EXAMPLE II 2-(1-(Ethoxyimino)propyl)-3-hydroxy-5-(3-oxo-(2H,4H)-1,4-benzoxazin-7-yl)cyclohex-2-en-1-one

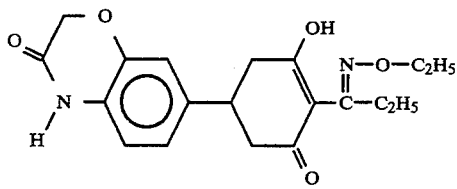

A solution of 0.9 g (2.9 mmol) of 2-propionyl-3-hydroxy-5-(3-oxo-(2H, 4H)-1,4-benzoxazin-7-yl)cyclohex-2-en-1-one in 20 mL of methyl sulfoxide was mixed with 0.30 g (3.1 mmol) of ethoxyamine hydrochloride and 0.30 g (3.7 mmol) of anhydrous sodium acetate. The resulting clear amber solution was stirred at ambient temperature under a nitrogen atmosphere for 16 hours. The mixture was diluted with 80 mL of water and the resulting solid precipitate collected by filtration. The solids were dissolved in 20 mL of dichloromethane, dried over MgSO$_4$ and filtered through a short column of silica gel. Evaporation off of the solvent gave the product as a white solid in a yield of 0.60 g (58 percent of theoretical). The title compound melted at 160.5°–162° C.; $^1$H NMR (CDCl$_3$): d1.00–1.38 (m, 6H, both —CH$_2$CH$_3$'s), 2.60–3.52 (m, 7H), 4.15 (q, J=7 Hz, 2H,—OCH$_2$CH$_3$), 4.65 (s, 2H, —OCH$_2$C=O), 6.80 (s, 3H, aromatic H's), 9.62 (broad s, 1H, —N—H), 14.5 (broad s, 1H, enol O—H); (Compound 2).

| Analysis: | percent | | |
|---|---|---|---|
| | C | H | N |
| Calc. for C$_{19}$H$_{22}$N$_2$O$_5$: | 63.67 | 6.19 | 7.82 |
| Found: | 63.58 | 6.17 | 7.76 |

EXAMPLE III 2-(1-(Ethoxyimino)propyl)-3-hydroxy-5-(N-methyl-3-oxo-(2H)-1,4-benzoxazin-6-yl)-cyclohex-2-en-1-one

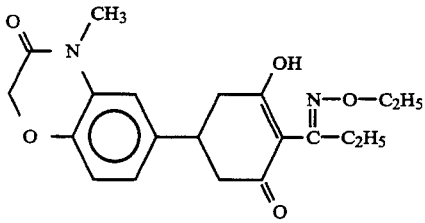

To 20 mL of methyl sulfoxide were added in sequence, 1.0 g (3.0 mmol) of 2-propionyl-3-hydroxy-5-(N-methyl-3-oxo-(2H)-1,4-benzoxazin-6-yl)cyclohex-2-en-1-one, 0.37 g (3.9 mmol) of ethoxyamine hydrochloride and 0.32 g (3.9 mmol) of anhydrous sodium acetate. The resulting mixture was stirred at ambient temperature for 5 hours, becoming a clear amber solution. The reaction mixture was diluted with 100 mL of water and extracted twice with 30 mL portions of ether. The extracts were combined, washed with water, then aqueous sodium chloride and dried over MgSO$_4$ and filtered. Evaporation off of the solvent gave the crude product as an oily residue which solidified upon standing. The crude solid was crushed and triturated in ether. The purified above-named product, as a tan solid, was recovered in a yield of 0.9 g (80 percent of theoretical). The title compound melted at 90°–92° C.; $^1$H NMR(CDCl$_3$): d1.05–1.48 (m, 6H, both —CCH$_2$CH$_3$'s), 2.55–3.62 (m including s at 3.31 for —N—CH$_3$, 1 OH) 4.18 (q, J=7 Hz, 2H,—OCH$_2$CH$_3$), 4.60 (s, 2H, —OCH$_2$C=O), 6.82–7.13 (m, 3H, aromatic H's), 15.10 (broad s, 1H, enol H); (Compound 3).

| Analysis: | percent | | |
|---|---|---|---|
| | C | H | N |
| Calc. for C$_{20}$H$_{24}$N$_2$O$_5$.0.2 H$_2$O: | 63.88 | 6.54 | 7.45 |
| Found: | 63.85 | 6.39 | 7.32 |

EXAMPLE IV 2-(1-(Ethoxyimino)propyl)-3-hydroxy-5-(N-cyanomethyl-3-oxo-(2H)-1,4-benzoxazin-6-yl)cyclohex-2-en-1-one

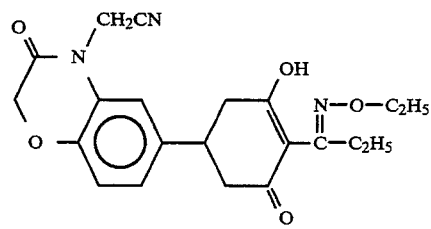

To 15 mL of methyl sulfoxide were added in sequence, 1.2 g (3.4 mmol) of 2-propionyl-3-hydroxy-5-(N-cyanomethyl-3-oxo-(2H)-1,4-benzoxazin-6-yl)cyclohex-2-en-1-one, 0.42 g (4.4 mmol) of ethoxyamine hydrochloride an d 0.36 g (4.4 mmol) of anhydrous sodium acetate. The resulting mixture was stirred at ambient temperature for 5 and ½ hours, becoming a clear amber solution. The reaction mixture was diluted with 100 mL of 0.1N HCl and extracted twice with 30 mL portions of ether. The extracts were combined, washed with water, then aqueous sodium chloride, dried over MgSO$_4$ and filtered. Evaporation off of the solvent gave the crude product as a light amber oil which solidified upon standing. The crude solid was triturated in warm ether and the product isolated by filtration as a tan solid. The product was recovered in a yield of 1.1 g (81 percent of theoretical) and melted at 156°–159° C.; $^1$H NMR(CDCl$_3$): d1.05–1.41 (m, 6H, both —CCH$_2$CH$_3$'s), 2.57–3.62 (m, 7H), 4.17 (q, J=7 Hz, 2H,—OCH$_2$CH$_3$), 4.70 (s, 2H, —OCH$_2$C=O), 4.88 (s, 2H, —NCH$_2$CN), 6.92–7.20 (m, 3H, aromatic H's), 15.10 (broad s, 1H, enol H); (Compound 4).

| Analysis: | percent | | |
|---|---|---|---|
| | C | H | N |
| Calc. for C$_{21}$H$_{23}$N$_3$O$_5$: | 63.46 | 5.83 | 10.57 |
| Found: | 63.59 | 5.97 | 10.17 |

EXAMPLE V 2-( 1-(Ethoxyimino)propyl )-3-hydroxy-5-(N-(2-propenyl)-3-oxo-(2H)-1,4-benzoxazin-6-yl)-cyclohex-2-en- 1-one

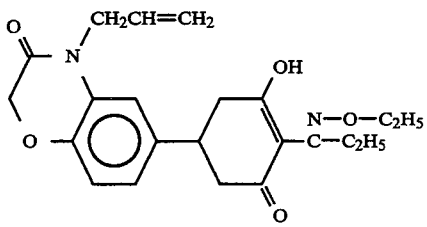

A solution of 1.3 g (3.7 mmol) of 2-propionyl-3-hydroxy-5-(N-(2-propenyl)-3-oxo-(2H)-1,4-benzoxazin-6-yl)cyclohex-2-en-1-one in 20 mL of methyl sulfoxide was treated with 0.43 g (4.5 mmol) of ethoxyamine hydrochloride and 0.36 g (4.4 mmol) of anhydrous sodium acetate. The resulting mixture was stirred at ambient temperature under a nitrogen atmosphere for 6 hours. The reaction mixture was diluted with 200 mL of water and extracted thrice with 20 mL portions of diethylether. The extracts were combined, washed with water, then aqueous sodium chloride, dried over MgSO$_4$ and filtered. Evaporation off of the solvent gave the crude product as a yellow oil which solidified upon standing. The resulting glassy solid was dissolved in a warm 1:1 ether-hexane solution. On cooling, the compound oiled out of the solution and again solidified and was isolated by filtration as a light tan solid. The product was recovered in a yield of 1.1 g (75 percent of theoretical) and melted at 79°-83° C.; $^1$H NMR(CDCl$_3$): d1.12 (t, J=7 Hz, 3H,—CCH$_2$CH$_3$), 1.32 (t, J=7 Hz, 3H,—OCH$_2$CH$_3$), 2.55-3.55 (m, 7H), 4.16 (q, J=7 Hz, 2H,—OCH$_2$CH$_3$), 4.50-4.70 (m including s at 4.60 for OCH$_2$C=O, 4H, —N—CH$_2$), 5.10-5.42 (m, 2H,—OCH=CH$_3$), 4.70 (s, 2H, —OCH$_2$-C=O), 4.88 (s, 2H, —NCH$_2$CN), 6.92-7.20 (m, 3H, aromatic H's), 15.10 (broad s, 1H, enol H); (Compound 5).

| Analysis: | percent | | |
|---|---|---|---|
| | C | H | N |
| Calc. for C$_{22}$H$_{26}$N$_2$O$_5$: | 66.31 | 6.58 | 7.03 |
| Found: | 66.57 | 6.68 | 6.82 |

EXAMPLE VI 2-(1-(Ethoxyimino)propyl)-3-hydroxy-5-(N-(2-chloroethyl)-3-oxo-(2H)-1,4-benzoaxazin-6-yl)cyclohex-2-en-1-one

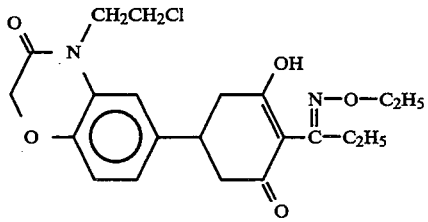

To 50 mL of absolute ethanol were added in sequence 1.0 g ( 2.6 mmol) of 2-propionyl-3-hydroxy-5-(N-(2-chloroethyl)-3-oxo-(2H)-1,4-benzoxazin-6-6l)cyclohex-2-en-1-one, 0.33 g (3.5 mmol) of ethoxyamine hydrochloride and 0.26 g (3.2 mmol) of anhydrous sodium acetate. The resulting mixture was stirred at ambient temperature for 3 hours. The reaction mixture was diluted with 500 mL of 0.5N HCl and extracted twice with 50 mL portions of ethyl acetate. The extracts were combined, dried over MgSO$_4$ and filtered. Evaporation off of the solvent gave the crude product as a pale oily residue. Flash chromatography on silica gel eluting with 15:85 acetone mixture afforded the above-named product as a clear colorless glass in a yield of 0.75 g (69 percent of theoretical). $^1$H NMR (CDCl$_3$): d1.07-1.45 (m, 6H, both —CH$_2$CH$_3$'s), 2.61-3.62 (m, 7H), 3.78 (t, J=7 Hz, 2H,—NCH$_2$), 4.00-4.45 (m, 4H,—OCH$_2$CH$_3$ and CH$_2$Cl), 4.63 (s, 2H, —OCH$_2$C=O), 6.85-7.13 (m, 3H, aromatic H's), 15.08 (broad s, 1H, enol H); (Compound 6).

| Analysis: | percent | | |
|---|---|---|---|
| | C | H | N |
| Calc. for C$_{21}$H$_{25}$ClN$_2$O$_5$: | 59.92 | 5.99 | 6.66 |
| Found: | 59.70 | 5.86 | 6.37 |

EXAMPLE VII 2-(1-(Ethoxyimino)propyl)-3-hydroxy-5-(N-benzyl-3-oxo-(2H)-1,4-benzoxazin-6-yl )-cyclohex-2-en-1-one

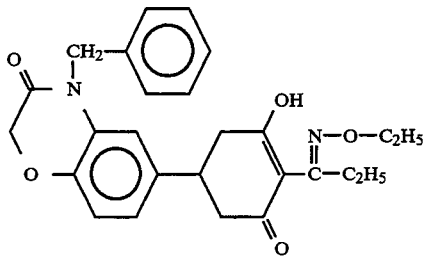

To 10 mL of methyl sulfoxide were added in sequence 1.4 g (3.5 mmol) of 2-propionyl-3-hydroxy-5-(N-benzyl-3-oxo-(2H)-1,4-benzoxazin-6-yl)cyclohex-2-en-1-one, 0.42 g (4.4 mmol) of ethoxyamine hydrochloride and 0.37 g (4.5 mmol) of anhydrous sodium acetate. The resulting mixture was stirred at ambient temperature for 3 hours. The reaction mixture was diluted with 50 mL of 0.5N HCl and extracted twice with 30 mL portions of ethyl acetate. The extracts were combined, dried over MgSO$_4$ and filtered. Evaporation off of the solvent gave an oily residue. The residue was dissolved in 50 mL of ether, washed with water, then an aqueous NaCl solution, dried over MgSO$_4$ and filtered. Evaporation off of the solvent gave a light amber glass which crystallized upon standing. The crude solid product was triturated in ether and the above-named product was isolated by filtration as a tan solid in a yield of 0.90 g (58 percent of theoretical). The product melted at 108°-110° C.; $^1$H NMR (CDCl$_3$): d1.05-1.41 (m, 6H, both —CH$_2$CH$_3$'s), 2.42-3.45 (m, 7H), 4.12 (q, J=7 Hz, 2H, —OCH$_2$CH$_3$), 4.72 (2, 2H, —OCH$_2$C=O), 5.20 (s, 2H, —CH$_2$Ph), 6.75-7.08 (m, 3H, aromatic H's), 7.30 (s, 5H, —CH$_2$Ph) ca. 14.7 (broad s, 1H, enol H); (Compound 7).

| Analysis: | percent | | |
|---|---|---|---|
| | C | H | N |
| Calc. for $C_{22}H_{28}N_2O_5$: | 69.62 | 6.29 | 6.25 |
| Found: | 70.01 | 6.26 | 6.26 |

EXAMPLE VIII 2-(1-(Ethoxyimino)propyl)-3-hydroxy-5-(N-methoxymethyl-3-oxo-(2H)-1,4-benzoxazin-6-yl)cyclohex-2-en-1-one

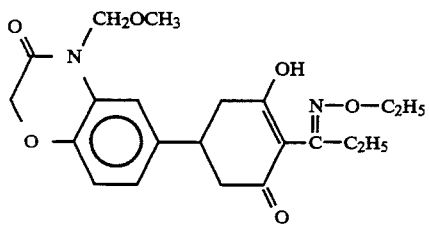

To 40 mL of absolute ethanol were added in sequence 0.90 g (2.5 mmol) of 2-propionyl-3-hydroxy-5-(N-methoxymethyl-3-oxo-(2H)-1,4 benzoxazin-6-yl)-cyclohex-2-en-1-one, 0.31 g (3.2 mmol) of ethoxyamine hydrochloride and 0.26 g (3.2 mmol) of anhydrous sodium acetate. The resulting mixture was stirred at ambient temperature for 3 hours. The reaction mixture was then partitioned between 200 mL of water and 50 mL of dichloromethane. The organic layer was separated, dried over MgSO₄ and filtered. Evaporation off of the solvent gave the crude product as an oily residue which crystallized upon standing. The crude solid was triturated in warm ether and the above-named product was isolated by filtration as a white solid which melted at 101°–103° C. in a yield of 0.60 g (60 percent of theoretical). ¹H NMR (CDCl₃): d1.05–1.52 (m, 6H, both —CH₂CH₃'s), 2.58–3.65 (m including 2H,OCH₂C=O), 5.33 (s, 2H, —NCH₂O), 6.85–7.30 (m, 3H, aromatic H's), 15.05 (broad s, 1H, enol H); (Compound 8).

| Analysis: | percent | | |
|---|---|---|---|
| | C | H | N |
| Calc. for $C_{21}H_{26}N_2O_6$: | 62.67 | 6.51 | 6.96 |
| Found: | 62.46 | 6.43 | 6.68 |

EXAMPLE IX 2-(1-(Ethoxyimino)propyl)-3-hydroxy-5-(N-(3-chloropropyl)-3-oxo-(2H)-1,4-benzoxazin-6-yl)cyclohex-2-en-1-one

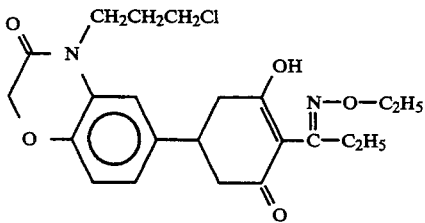

To 50 mL of absolute ethanol were added in sequence 1.6 g (4.1 mmol) of 2-propionyl-3-hydroxy-5-(N-(3-chloropropyl)-3-oxo-(2H)-1,4-benzoxazin-6-yl)-cyclohex-2-en-1-one, 0.32 g (3.4 mmol) of ethoxyamine hydrochloride and 0.27 g (3.3 mmol) of anhydrous sodium acetate. The resulting mixture was stirred at ambient temperature for 2.5 hours. The reaction mixture was then diluted with 200 mL of water and extracted twice with 50 mL portions of dichloromethane. The extracts were combined, dried over MgSO₄ and filtered. Evaporation off of the solvent gave the crude product as a yellow oily residue. Flash chromatography on silica gel eluting with 20 percent acetone/hexane afforded the above-named product as a pale glassy oil in a yield of 1.0 g (56 percent of theoretical). ¹H NMR (CDCl₃): d1.05–1.43 (m, 6H, both —CH₂CH₃'s), 2.15 (p, J=7 Hz, 2H,—CH₂CH₂Cl and —CH₂Cl), 4.57 (s, 2H, —OCH₂-C=O), 6.83–7.00 (m, 3H, aromatic H's), 14.9 (broad s, 1H, enol H); (Compound 9).

| Analysis: | percent | | |
|---|---|---|---|
| | C | H | N |
| Calc. for $C_{22}H_{27}ClN_2O_5$: | 60.75 | 6.26 | 6.44 |
| Found: | 60.92 | 6.08 | 6.37 |

EXAMPLE X 2-(1-(Ethoxyimino)-propyl)-3-hydroxy-5-(2-methyl-3-oxo-(2H, 4H)-1,4-benzoxazin-6-yl)cyclohex-2-en-1-one

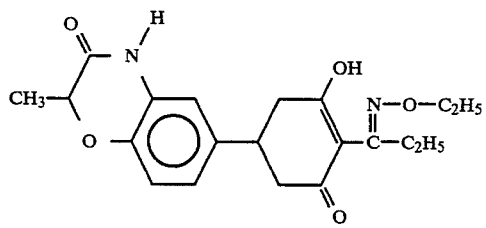

A slurry of 1.0 g (3.0 mmol) of 2-(1-propionyl)-3-hydroxy-5-(2-methyl-3-oxo-(2H,4H)-1,4-benzoxazin-6-yl)cyclohex-2-en-1-one in 35 mL of absolute ethanol was treated with 0.37 g (3.9 mmol) of ethoxyamine hydrochloride and 0.32 g (3.9 mmol) of anhydrous sodium acetate. The resulting heterogeneous mixture was stirred at ambient temperature for 6 hours. The reaction mixture was then diluted with mL of 0.2N HCl and extracted twice with 30 mL portions of dichloromethane. The extracts were combined, dried over MgSO₄ and filtered. Evaporation off of the solvent gave the crude product as a solid residue. The solid was triturated in warm ether and filtered to afford the above-named product as a beige solid which melted at 144°–146° C. in a yield of 0.90 g (81 percent of theoretical). ¹H NMR (CDCl₃): d1.05–1.50 (m, 6H, —N=C=CH₂CH₃ and OCH₂CH₃), 2.61–3.56 (m, 7H), 4.18 (q, J=7 Hz, 2H,—OCH₂CH₃), 4.71 (q, J=8 Hz, 1H,—OCHC=O), 6.72–7.05 (m, 3H, aromatic H's), 9.80 (broad s, 1H, —N—H), 15.1 (broad s, 1H, enol —O—H); (Compound 10).

| Analysis: | percent | | |
|---|---|---|---|
| | C | H | N |
| Calc. for $C_{20}H_{24}N_2O_5$: | 64.50 | 6.50 | 7.52 |
| Found: | 64.56 | 6.49 | 7.10 |

EXAMPLE XI 2-(1-(Ethoxyimino)propyl)-3-hydroxy-5-(N-(2-propynyl)-3-oxo-(2H)-1,4-benzoxazin-6-yl)cyclohex-2-en-1-one

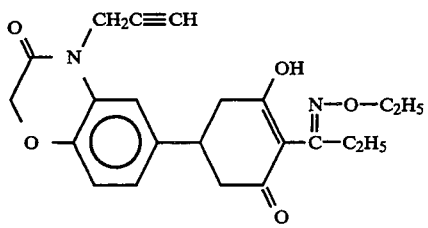

To 50 mL of methyl sulfoxide were added in sequence 2.2 g (6.2 mmol) of 2-propionyl-3-hydroxy-5-(N-(2-propynyl)-3-oxo-(2H)-1,4-benzoxazin-6-yl)cyclohex-2-en-1-one, 0.70 g (7.4 mmol) of ethoxyamine hydrochloride and 0.60 g (7.3 mmol) of anhydrous sodium acetate. The resulting mixture was stirred at ambient temperature for 3.5 hours. The reaction mixture was then diluted with 400 mL of 0.2N HCl and extracted four times with 20 mL portions of dichloromethane. The extracts were combined, washed with aqueous NaCl, dried over MgSO$_4$ and filtered through a short pad of silica gel. Evaporation off of the solvent gave the crude product as a light yellow glass, which solidified upon standing. The solid was triturated in ether and the product isolated by filtration which afforded the above-named product as a white solid which melted at 100°–102° C. in a yield of 1.3 g (53 percent of theoretical). $^1$H NMR (CDCl$_3$): d1.08–1.47 (m, 6H, both —CH$_2$CH$_3$'s), 2.31 (t, J=2 Hz, 1H,—C—CH), 2.62–3.64 (m, 7H), 4.17 (q, J=7 Hz, 2H, OCH$_2$CH$_3$), 4.67 (s, 2H, —OCH$_2$C=O), 4.74(d, J=2 Hz, 2H,—NCH$_2$), 6.87–7.12 (m, 3H, aromatic H's), 15.10 (broad s, 1H, enol H); (Compound 11).

| Analysis: | percent | | |
|---|---|---|---|
| | C | H | N |
| Calc. for C$_{22}$H$_{24}$N$_2$O$_5$: | 66.65 | 6.10 | 7.07 |
| Found: | 66.30 | 6.35 | 7.04 |

EXAMPLE XII 2-(1-(Ethoxyimino)propyl)-3-hydroxy-5-(N-(3-methylpropyl)-3-oxo-(2H)-1,4-benzoxazin-6-yl)cyclohex-2-en-1-one

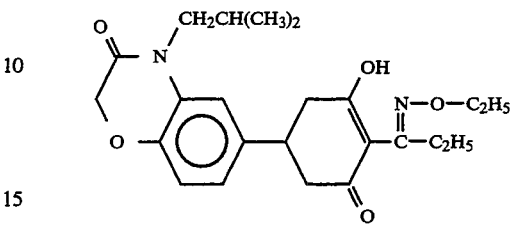

To 125 mL of absolute ethanol were added in sequence 1.5 g (4.0 mmol) of 2-propionyl-3-hydroxy-5-(N-(3-methylpropyl)-3-oxo-(2H)-1,4-benzoxazin-6-yl)-cyclohex-2-en-1-one, 0.50 g (5.2 mmol) of ethoxyamine hydrochloride and 0.40 g (4.9 mmol) of anhydrous sodium acetate. The resulting mixture was stirred at ambient temperature for 16 hours. The reaction mixture was then diluted with 400 mL of 0.1N HCl and extracted twice times with 50 mL portions of dichloromethane. The extracts were combined, dried over MgSO$_4$ and filtered. Flash chromatography on silica gel eluting with 10 percent acetone/hexane afforded the above-named product as a clear glassy oil in a yield of 1.3 g (78 percent of theoretical). E$^1$H NMR (CDCl$_3$): d0.85–1.50 (m including d, 6H, J=7 Hz, at 0.96 for —CH(CH$_3$)$_2$, 12H, both —CH$_2$CH$_3$'s), 1.87–2.37 (m, 1H,—CH(CH$_3$)$_2$), 2.61–3.62 (m, 7H), 3.85 (d, J=7 Hz, 2H, —NCH$_2$), 4.18 (q, J=7 Hz, 2H, —OCH$_2$CH$_3$), 4.64(s, 2H, —OCH$_2$C=O), 6.83–7.12 (m, 3H, aromatic H's), 15.10 (broad s, 1H, enol H); (Compound 12).

| Analysis: | percent | | |
|---|---|---|---|
| | C | H | N |
| Calc. for C$_{23}$H$_{30}$N$_2$O$_5$: | 66.64 | 7.30 | 6.76 |
| Found: | 66.40 | 7.72 | 6.81 |

By following the hereinabove procedures of the above set forth examples, employing the appropriate starting cyclohex-2-en-1-one and amine reactants, the following compounds in Table III are prepared.

TABLE III

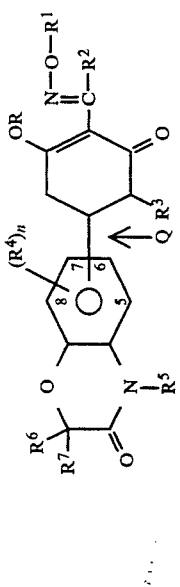

Q = point of attachment to ring

| Cmpd No. | R | R¹ | R² | R³ | (R⁴)ₙ | R⁵ | R⁶ | R⁷ | Q | M.P. °C. | Elem. Analysis Calc'd/Found C | H | N |
|---|---|---|---|---|---|---|---|---|---|---|---|---|---|
| 10-R | —H | ethyl | ethyl | —H | —H | —H | (R)-methyl | —H | 6 | 147–149 | 64.50 / 64.59 | 6.50 / 6.71 | 7.52 / 7.30 |
| 10-S | —H | ethyl | ethyl | —H | —H | —H | (S)-methyl | —H | 6 | 144–146.5 | 64.50 / 64.43 | 6.50 / 6.40 | 7.52 / 7.31 |
| 13 | —H | ethyl | ethyl | —H | —H | methyl | methyl | —H | 6 | oil | 65.27 / 65.32 | 6.78 / 6.88 | 7.25 / 7.61 |
| 14 | —H | ethyl | ethyl | —H | —H | —CH₂CH=CH₂ | methyl | —H | 6 | oil | 66.97 / 67.17 | 6.84 / 7.07 | 6.79 / 6.69 |
| 15 | —H | ethyl | ethyl | —H | —H | —(CH₂)₂Cl | methyl | —H | 6 | oil | 60.75 / 60.83 | 6.26 / 6.34 | 6.44 / 6.36 |
| 16 | —H | ethyl | ethyl | —H | —H | —(CH₂)₂OH | methyl | —H | 6 | oil | 62.10ᵃ / 62.12ᵃ | 6.87ᵃ / 6.46ᵃ | 6.59ᵃ / 6.71ᵃ |
| 17 | —H | ethyl | ethyl | —H | —H | —H | —H | —H | 6 | 138–139.5 | 64.85 / 64.72 | 5.99 / 6.15 | 7.56 / 7.52 |
| 18 | —H | —CH₂CH=CH₂ | -n-propyl | —H | —H | —H | —H | —H | 6 | 142.6–143.5 | 64.50 / 64.85 | 6.50 / 6.71 | 7.52 / 7.51 |
| 19 | —H | ethyl | -n-propyl | —H | —H | —H | —H | —H | 6 | 128–128.6 | 65.61 / 65.58 | 6.29 / 6.48 | 7.29 / 7.25 |
| 20 | —H | —CH₂CH=CH₂ | ethyl | —H | —H | —H | —H | —H | 6 | 142–144.5 | 59.33 / 59.49 | 5.23 / 5.34 | 6.92 / 6.72 |
| 21 | —H | trans- —CH₂CH=CHCl | -n-propyl | —H | —H | —H | —H | —H | 6 | 152–155 | 60.21 / 60.09 | 5.53 / 5.69 | 6.69 / 6.61 |
| 22 | —H | trans- —CH₂CH=CHCl | methyl | —H | —H | —H | —H | —H | 6 | 167–169 | 64.03 / 64.20 | 5.66 / 5.91 | 7.86 / 8.21 |
| 23 | —H | trans- —CH₂CH=CHCl | methyl | —H | —H | —H | —H | —H | 6 | 159–162 | 58.39 / 58.12 | 4.90 / 4.97 | 7.17 / 7.42 |
| 24 | —H | ethyl | ethyl | —H | —H | —H | —H | —H | 6 | 178–181 (dec.) | 62.78 / 62.78 | 5.85 / 6.23 | 8.14 / 8.45 |
| 25 | —H | ethyl | ethyl | —H | —H | —H | ethyl | —H | 6 | 143–145 | 65.26 / 65.59 | 6.78 / 7.01 | 7.25 / 6.87 |
| 26 | —H | ethyl | ethyl | —H | —H | —H | phenyl | —H | 6 | 201–203 | 69.11 / 69.35 | 6.03 / 6.33 | 6.45 / 6.15 |
| 27 | —H | ethyl | ethyl | —H | —H | trans- —CH₂CH=CHCl | —H | —H | 6 | 118–120 | 61.04 / 61.15 | 5.82 / 6.00 | 6.47 / 6.46 |
| 28 | —H | ethyl | ethyl | —H | —H | —H | —OCH(CH₃)₂ | —H | 6 | 132–135 | 61.66ᵇ / 61.70ᵇ | 6.90ᵇ / 6.81ᵇ | 6.54ᵇ / 6.47ᵇ |
| 29 | —H | ethyl | -n-propyl | —H | —H | —H | methyl | —H | 6 | 133–135 | 65.27 | 6.78 | 7.25 |

TABLE III-continued

[Structure shown with substituents R, OR, N-O-R¹, C-R², R³, (R⁴)ₙ, R⁵, R⁶, R⁷, and positions 5,6,7,8 on ring]

Q = point of attachment to ring

| Cmpd No. | R | R¹ | R² | R³ | (R⁴)ₙ | R⁵ | R⁶ | R⁷ | Q | M.P.°C. | Elem. Analysis Calc'd/Found C | H | N |
|---|---|---|---|---|---|---|---|---|---|---|---|---|---|
| 30 | —H | trans- —CH₂CH=CHCl | -n-propyl | —H | —H | —H | methyl | —H | 6 | 117-121 | 65.02 / 61.04 | 6.72 / 5.82 | 7.05 / 6.47 |
| 31 | —H | ethyl | ethyl | —H | 7-methyl | —H | methyl | —H | 6 | 1.82-1.84.5 | 60.80 / 65.27 | 5.87 / 6.78 | 6.56 / 7.25 |
| 32 | —H | ethyl | ethyl | —H | —H | —H | methyl | —H | 7 | 159-160 | 65.33 / 64.50 | 7.01 / 6.50 | 6.96 / 7.52 |
| 33 | —H | ethyl | ethyl | —H | —H | —H | —CH₂OC₂H₅ | —H | 6 | 161.5-163 (dec.) | 64.46 / 63.45 | 6.69 / 6.78 | 7.38 / 6.73 |
| 34 | —H | ethyl | ethyl | —H | —H | —H | R⁶, R⁷ together is =CH₂ | — | 6 | 144-146 (dec.) | 63.69 / — | 6.69 / — | 6.49 / — |
| 35 | —H | ethyl | ethyl | —H | —H | —H | —CH₂OCH₃ | —H | 6 | 150-151.5 (dec.) | 62.70 / 63.16 | 6.51 / 6.65 | 6.96 / 7.22 |
| 36 | —H | ethyl | ethyl | —H | —H | —H | -n-propyl | —H | 6 | 194-196 | 66.00 / 65.87 | 7.05 / 7.22 | 7.00 / 7.00 |
| 37 | —H | ethyl | ethyl | —H | —H | —H | —OCH₃ | —H | 6 | 150-151.5 (dec.) | 62.70 / 63.16 | 6.51 / 6.65 | 6.96 / 7.22 |
| 38 | —H | ethyl | ethyl | —H | —H | —H | methyl | methyl | 6 | 140-141 (dec.) | 65.27 / 65.01 | 6.78 / 6.81 | 7.25 / 7.06 |
| 39 | —H | ethyl | ethyl | —H | 7-Cl | —H | methyl | —H | 6 | 177 | 59.04 / 58.82 | 5.70 / 5.68 | 6.89 / 6.85 |
| 40 | —H | trans- —CH₂CH=CHCl | ethyl | —H | —H | —H | methyl | methyl | 6 | 130-132 | 58.60ᶜ / 58.25ᶜ | 6.04ᶜ / 5.57ᶜ | 6.21ᶜ / 6.10ᶜ | a = calculated as a 0.50 H₂O hydrate.
b = calculated as a 0.67 H₂O hydrate.
c = calculated as a 1.00 H₂O hydrate.

EXAMPLE XIII

2-Propionyl-3-hydroxy-5-(3-oxo-(2H, 4H)-1,4-benzoxazin-6-yl)cyclohex-2-en-1-one

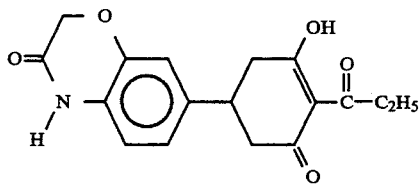

A solution of sodium ethoxide was prepared by dissolving 1.5 g (0.065 mol) of sodium metal in 250 mL of absolute ethanol. To this solution was added 9.6 g (0.027 mol) of 2-propionyl-3-hydroxy-5-(3-(N-2-chloroacetyl)amino-4-hydroxyphenyl)cyclohex-2-en-1-one in solid portions. The mixture was heated at reflux for 45 minutes, cooled to room temperature and poured into 600 mL of ice cold 0.2N HCl. The precipitate which formed was recovered by filtration to give the above-named product, as a light gray solid, in a yield of 7.9 g (93 percent of theoretical). The product melted at 207.5°–210° C.; $^1$H NMR (1:1 CDCl$_3$-DMSO-d$_6$): d1.08 (t, J=7 Hz, 3H, —CH$_3$), 2.52–3.70 (m, 7H), 4.52 (s, 2H, —CH$_2$), 6.86 (s, 3H, aromatic H's), 10.55 (broad s, 1H, —N—H), enol O—H not observed.

EXAMPLE XIV

2-Propionyl-3-hydroxy-5-(N-(2-propenyl)-3-oxo-(2H, 4H)-1,4-benzoxazin-6-yl )-cyclohex-2-en-1-one

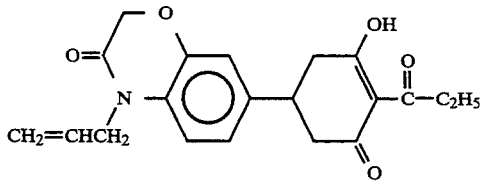

Sixty percent sodium hydride in mineral oil 0.60 g (15 mmol NaH) was washed once with 15 mL of hexane, decanting via pipette. To this was added 1.6 g (5.1 mmol) of 2-propionyl-3-hydroxy-5-(3-oxo-(2H, 4H)-1,4-benzoxazin-6-yl)cyclohex-2-en-1-one in solid portions. The mixture was stirred at room temperature for 15 minutes, treated with 1.4 g (12 mmol) of allyl bromide and stirred at room temperature for 30 minutes. The mixture was poured into 100 mL of ice cold 0.2N HCl and extracted twice with 30 mL portions of a 5:1 ether-ethyl acetate mixture. The extracts were combined, washed with water, an aqueous NaCl solution, dried over MgSO$_4$, filtered and the solvent evaporated off to give the crude product, as a yellow solid. Recrystallization from ethanol afforded the above-named product in a yield of 1.4 g (77 percent of theoretical). The product melted at 129°–131.5° C.; $^1$H NMR (CDCl$_3$): d1.10 (t, J=7 Hz, 3H, —CH$_3$), 2.55–3.56 (m, 7H), 4.52–4.73 (m including s at 4.50 for OCH$_2$, 4H, —NCH$_2$), 5.12–5.42 (m, 2H, —CH=CH$_2$), 5.70–6.15 (m, 1H, —CH=CH$_2$), 6.82–7.10 (m, 3H, aromatic H's), 18.10 (broad s, 1H, enol O—H).

| Analysis: | percent | | |
|---|---|---|---|
| | C | H | N |
| Calc. for C$_{20}$H$_{21}$NO$_5$: | 67.59 | 5.96 | 3.94 |
| Found: | 67.21 | 5.96 | 3.77 |

The compounds of the present invention have been found to be suitable for use in methods for the pre- and postemergent control of many annual and perennial grassy weeds,. In addition, certain of the present compounds are sufficiently tolerated by most broadleaf crops, such as, for example, soybeans, cotton and sugarbeet to allow for the postemergent control of grassy weeds growing among said crops. Further, certain of the compounds are sufficiently tolerated by certain grass crops, such as, for example, corn to allow for the postemergent control of grassy weeds growing among said crop.

It is to be noted that while all compounds have herbicidal activity, each compound/active ingredient may have a slightly different degree of herbicidal activity on different plants. Some compounds may be more active in the control of one specific weed species than another and some compounds may be more selective toward one crop species than another. Many of these compounds are unique because of their systemic action and because of the very low levels of chemical required to control the grassy weeds.

For such uses, unmodified active ingredients of the present invention can be employed. However, the compounds may be prepared in formulations/compositions as dusts, wettable powders, flowable concentrates, or emulsifiable concentrates by the admixture of the active compounds with inert materials, known in the art as inert agricultural adjuvants and/or carriers, in solid or liquid form.

Thus, for example, the active compound(s) can be admixed with one or more additives including organic solvents, petroleum distillates, water or other liquid carriers, surface active dispersing agents, and finely-divided inert solids. For example, an active ingredient can be dispersed on a finely-divided solid and employed herein as a dust or granule. Also, the active ingredients, as liquid concentrates or solid compositions comprising one or more of the active ingredients, can be dispersed in water, typically with aid of a wetting agent, and the resulting aqueous dispersion employed as a spray. In other procedures, the active ingredients can be employed as a constituent of organic liquid compositions, oil-in-water and water-in-oil emulsions or water dispersions, with or without the addition of wetting, dispersing, or emulsifying agents.

The herbicidally effective concentration of the active ingredients in solid or liquid compositions generally is from about 0.0003 to about 95 percent by weight or more. Concentrations from about 0.05 to about 50 percent by weight are often employed.

The compound can be employed in the form of diluted flowable compositions or a wettable powder composition containing 2 to 10,000 ppm of one or more of the compounds, preferably 10 to 600 ppm are employed. When the carrier contains a surface active agent, from about 0.1 to about 20 percent by weight of the active ingredient is advantageously employed. Depending upon the concentration in the composition, such augmented compositions are adapted to be employed for the control of the undesirable plants or employed as concentrates and subsequently diluted with additional inert carrier, e.g., water to produce the ultimate treating compositions.

Similarly, the toxicant products can be compounded with a suitable water-immiscible inert organic liquid and a surface active dispersing agent to produce an emulsifiable concentrate which can be further diluted with water and oil to form spray mixtures in the form of oil-in-water emulsions which may optionally contain water miscible organic co-solvents to improve the physical properties of the formulation. In such compositions, the carrier comprises an aqueous emulsion, i.e., a mixture of inert water-immiscible solvent and optional water miscible organic co-solvent, emulsifying agent and water. In such compositions, the active ingredient is usually present in a concentration from about 5 to about 98 weight percent.

In the preparation of dust, or wettable powder compositions, the toxicant products can be compounded with any of the finely-divided solids, such as prophyllite, talc, chalk, gypsum, fuller's earth, bentonitc, attapulgite, starch, casein, gluten, or the like. In such operations, the finely-divided carrier is ground or mixed with the toxicant or wet with a solution of the toxicant in a volatile organic solvent. Also, such compositions when employed as concentrates can be dispersed in water, with or without the aid of dispersing agents to form spray mixtures. With dusts, good results can usually be obtained employing compositions containing from about 0.1 to about 2.0 percent or more by weight of toxicant.

Granular formulations are usually prepared by impregnating a solution of the toxicant in a volatile organic solvent onto a bed of coarsely-divided attapulgite, bentonitc, diatomite, or the like.

Emulsifiers which can be advantageously employed herein can be readily determined by those skilled in the art and include various nonionic, anionic and cationic emulsifiers, or a blend of two or more of said emulsifiers.

Examples of nonionic emulsifiers useful in preparing the emulsifiable concentrates include the polyalkylene glycol ethers and condensation products of alkyl and aryl phenols, aliphatic alcohols, aliphatic amines or fatty acids with ethylene oxide, propylene oxide or mixtures of ethylene and propylene oxides such as the ethoxylated alkyl phenols and carboxylic esters solubilized with the polyol or polyoxyalkylene.

Anionic emulsifiers include the oil-soluble salts (e.g., calcium) of alkylaryl sulphonic acids, oil soluble salts of sulphated polyglycol ethers and appropriate salts of phosphated polyglycol ether. Cationic emulsifiers include quaternary ammonium compounds and fatty amines.

The preferred emulsifiers will depend upon the nature of the emulsifiable concentrate. For example, an emulsifiable concentrate of a compound of Formula I containing 200 g/L of the compound in xylene may require a blend of an ethoxylated nonyl phenol and calcium dodecyl benzene sulphonate to function effectively, whereas a similar emulsifiable concentrate of the oleate salt of a compound of Formula I soluble in an aliphatic organic solvent will require a considerably different emulsification system.

Representative organic liquids which can be employed in preparing the emulsifiable concentrates of the present invention are the aromatic liquids such as xylene; propyl benzene fractions; or mixed naphthalene fractions; mineral oils substituted aromatic organic liquids such as dioctyl phthalate; kerosene; butene; dialkyl amides of various fatty acids, particularly the dimethyl amides of fatty glycols and glycol derivatives such as the n-butyl ether, ethyl ether or methyl ether of diethylene glycol, the methyl ether of triethylene glycol. Mixtures of two or more organic liquids are also often suitably employed in the preparation of the emulsifiable concentrate. The preferred organic liquids are xylene, and propyl benzene fractions, with xylene being most preferred.

The surface active dispersing agents are usually employed in liquid compositions and in the amount of from 0.1 to 20 percent by weight of the combined weight of the dispersing agent and active compound.

Especially, these active compositions may contain adjuvant surfactants to enhance the deposition, wetting and penetration of the composition onto the target crop and organism. These adjuvant surfactants may optionally be employed as a component of the formulation or as a tank mix. The amount of adjuvant surfactant will vary from 0.01 percent to 2.0 percent v/v based on a spray-volume of water, preferably 0.05 to 0.5 percent. Suitable adjuvant surfactants include ethoxylated nonyl phenols, ethoxylated synthetic or natural alcohols, salts of the esters of sulphosuccinic acids, ethoxylated organosilicones, ethoxylated fatty amines and blends of surfactant with mineral or vegetable oils.

In further embodiments, the compounds of the present invention or compositions containing the same, can be advantageously employed in combination with one or more additional pesticidal compounds. Such additional pesticidal compounds may be insecticides, nematocides, miticides, arthropodicides, herbicides, fungitides or bactericides that are compatible with the compounds of the present invention in the medium selected for application and not antagonistic to the activity of the present compounds. Accordingly, in such embodiments, the pesticidal compound is employed as a supplemental toxicant for the same or for a different pesticidal use or as an additament. The compounds in combination can generally be present in a ratio of from 1 to 100 parts of the compound of the present invention with from 100 to 1 part of the additional compound(s).

The active ingredients of the present invention have been found to possess desirable postemergent activity against grassy weeds such as foxtail, barnyard grass, wild oat, Johnson grass and the like, while showing high selectivity to important broadleaf crops such as cotton, sunflower, sugarbeet, rape and soybeans and grassy crops such as corn. These compounds are also effective in selectively controlling perennial grassy weeds such as Johnson grass and the like in the presence of said crop plants.

The exact amount of the active material to be applied is dependent not only on the specific active ingredient being applied, but also on the particular action desired, the plant species to be controlled and the stage of growth thereof as well as the part of the plant to be contacted with the toxic active ingredient. Thus, all of the active ingredients of the present invention and compositions containing the same may not be equally effective at similar concentrations or equally effective against the same plant species.

In preemergent operations a dosage rate of 0.01 to 10 lbs/acre (0.011 to 11.2 kgs/hectare), preferably 0.05 to 2.0 lbs/acre (0.056 to 2.25 kgs/hectare) and most preferably 0.1 to 1 lb/acre (0.11 to 1.12 kgs/hectare) is generally employed.

In postemergent operations a dosage of about 0.01 to about 20 lbs/acre (0.056–22.4 kg/hectare) is generally applicable, although not all compounds are equally effective and some weeds are more difficult to control. Thus, a dosage rate in the range of about 0.01 to about 1.0 lb/acre (0.01–1.12 kg/hectare) is preferred in postemergent control of annual grassy weeds, while about 0.05 to about 5 lbs/acre (0.056–5.6 kg/hectare) is a preferred dosage range for the postemergent control of perennial grassy weeds. In applications to tolerant crops a weed controlling but less than crop damaging amount of from about 0.005 to about 1.0 lb/acre (0.0056 to 1.12 kgs/hectare) is generally employed.

Representative formulations/compositions of the present invention include the following:

TABLE IV
Emulsifiable Concentrate

| Ingredient | weight percent of total composition |
|---|---|
| Compound No. 3 | 6.4 |
| Atlox TM 3454a | 5.4 |
| Atlox TM 3413a | 5.4 |
| Aromatic 100 | 41.4 |
| Cyclohexanone | 41.4 |

TABLE V

| Ingredient | weight percent of total composition |
|---|---|
| Compound No. 4 | 5.0 |
| Xylene | 65.0 |
| Hallcomid TM M8-10[b] | 20.0 |
| Tenseofix TM B7438[c] | 3.0 |
| Tenseofix TM B7453[c] | 3.0 |
| Ethomeen TM C25[d] | 4.0 |

TABLE VI
Wettable Powder

| Ingredient | weight percent of total composition |
|---|---|
| Compound No. 3 | 25.0 |
| Barden AG clay | 50.0 |
| Celite TM 209[e] | 17.0 |
| Nekal TM BA-75[f] | 3.0 |
| Daxad TM 21[g] | 5.0 |

TABLE VII

| Ingredient | weight percent of total composition |
|---|---|
| Compound No. 4 | 50.0 |
| Barden AG clay | 21.0 |
| Celite TM 209[e] | 21.0 |
| Polyfon TM H[h] | 5.0 |
| Aerosol TM OTB[i] | 3.0 |

TABLE VIII
Flowable Concentrate

| Ingredient | weight percent of total composition |
|---|---|
| Compound No. 3 | 12.0 |
| Pluronic TM P105[j] | 2.0 |
| Darvan TM #1[k] | 0.5 |
| Dow Corning FG10[m] | 1.0 |
| VeeGum TM [n] | 0.3 |
| Kelzan TM [o] | 0.04 |
| Propylene glycol | 4.5 |
| water | 79.66 |

TABLE IX

| Ingredient | weight percent of total composition |
|---|---|
| Compound No. 4 | 12.0 |
| Sun Spray TM 11N oil[p] | 72.7 |
| Bentone TM 38[q] | 1.0 |
| solution of 95% methanol/5% water | 0.3 |
| Emulsogen TM M[r] | 12.0 |
| Agrimul TM 70A[s] | 2.0 |

TABLE X
Dusts

| Ingredient | weight percent of total composition |
|---|---|
| Compound No. 3 | 5.0 |
| Barden clay | 80.0 |
| Celite TM 209[e] | 15.0 |

TABLE XI

| Ingredient | weight percent of total composition |
|---|---|
| Compound No. 4 | 2.5 |
| Barden clay | 82.5 |
| Celite TM 209[e] | 15.0 |

In the above Tables:

Aromatic 100 = an aromatic hydrocarbon solvent with a Flash point above 101° F.TCC, a product of Exxon Corp.

a = an anionic/nonionic emulsifier product of Atlas Chemical Industries, Inc.

b = N,N'-dimethyl amides of fatty acid, a product of The C. P. Hall Co.

c = blends of calcium dodecylbenzenesulfonates with nonylphenol propylene oxide/ethylene oxide block copolymers, a product, of Tenseia, Inc.

d = is a proprietary material of Akzo Chemicals, Inc.

e = diatomaceous earth, a product of Johns-Manville Products, Inc.

f = sodium alkylnaphthalene sulfonate, an anionic emulsifier product of GAF Corp.

g = a polyaryl and substituted benzoid alkylsulfonic acid, a product of W. R. Grace & Co.

h = sugar-free, sodium based sulfonates of Kraft lignin is a proprietary material of West Virginia Pulp and Paper Co.

i = dioctyl ester of sodium sulfosuccinic acid, a product of American Cyanamid Co.

j = condensate of ethylene oxide with hydrophobic bases formed by condensing propylene oxide with propylene glycol, a product of BASF Corp.

k=sodium salts of polymerized alkylnaphthalene sulfonic acid, an anionic surfactant of R. T. Vanderbilt Co., Inc.

m=is a proprietary material of Dow Corning Corp.

n=colloidal magnesium aluminum silicate, a product of R. T. Vanderbilt Co., Inc.

o=a polysaccharide known as xanthan gum, a product of Kelco Co.

p=a phytobland mineral oil also known as spray oil, a product of Sun Oil Co.

q=organic derivative of hydrous magnesium aluminum silicate minerals, a product of National Lead Co.

r=a nonionic ethoxylated derivative-a mineral oil emulsifier of American Hoechst Corp.

s=alkyl aryl polyether alcohol, a product of Henkel Corp.

The following examples illustrate the herbicidal effects of the compounds of this invention.

The plant species employed in these evaluations were as follows:

TABLE XII

| Common Name | Scientific Name |
| --- | --- |
| Barnyardgrass | Echinochloa crusgalli |
| Broadleaf signalgrass | Brachiaria platyphylla |
| Corn | Zea maize |
| Cotton | Gossypium hirsutum |
| Crabgrass | Digitaria sanguinalis |
| Fall Panicum | Panicum dichotomiflorum |
| Giant Foxtail | Setaria faberi |
| Green Foxtail | Setaria viridis |
| Johnsongrass | Sorghum halepense |
| Wild Oat | Avena fatua |
| Oilseed rape | Brassica napus |
| Sorghum | Sorghum bicolor |
| Soybean | Glycine max |
| Sugarbeet | Beta vulgaris |
| Sunflower | Helianthus annuus |
| Yellow Foxtail | Setaria lutescens |

EXAMPLE XV

Postemergent Evaluation

In representative operations, each compound to be utilized in a series of tests is dissolved in acetone to one-half of the final volume (twice the final concentration) to be used and the acetone solution in each case is admixed with an equal volume of an aqueous solution composed of 78 percent water, 20 percent isopropanol, 2 percent Atplus TM 411f (a proprietary crop oil material of ICI Americas Inc., Wilmington, Del.) and 0.04 percent Triton TM X-155 (a nonionic surfactant which is an alkylaryl polyether alcohol, a proprietary material of Union Carbide Chem. & Plastic Co., Danbury, Conn.). The compositions, generally in the nature of an emulsion, were employed to spray separate respective plant species which had been grown in a greenhouse to a height of 2–6 inches in soil of good nutrient content. Sufficient amounts were employed to provide various application rates as listed in the table. The various beds were positioned side by side and exposed to substantially identical conditions of temperature and light. Each bed was maintained so as to prevent any interaction with test compounds in different plant beds. Other plant beds were treated with an isopropanol/Atplus TM 411f/Triton TM X-155/water mixture containing no test compound to serve as controls. After treatment, the plants were maintained for about 2 weeks under greenhouse conditions conducive for good plant growth and watered as necessary. The specific plant species, test compound and dosage and the percent postemergent control obtained are set forth in Table XIII. Control refers to the reduction in growth compared to the observed results of the same untreated species. Note the "NT" means "not tested."

TABLE XIII

| Compound Tested | Dosage in PPM | Percent Kill and Control of Plant Species | | | | | | | |
| --- | --- | --- | --- | --- | --- | --- | --- | --- | --- |
| | | Cotton | Rape | Soybean | Sugarbeet | Giant Foxtail | Johnson Grass | Barnyard Grass | Wild Oat |
| 1 | 125 | 0 | 0 | 0 | 0 | 100 | 100 | 100 | 100 |
| 2 | 125 | 0 | 0 | 0 | 0 | 100 | 100 | 100 | 90 |
| 3 | 125 | 0 | 0 | 0 | 0 | 80 | 100 | 100 | 100 |
| 4 | 125 | 0 | 0 | 0 | 0 | 90 | 90 | 100 | 100 |
| 5 | 125 | 0 | 0 | 0 | 0 | 85 | 100 | 98 | 85 |
| 6 | 125 | 0 | 0 | 0 | 0 | 95 | 100 | 100 | 90 |
| 7 | 125 | 0 | 0 | 0 | 0 | 65 | 70 | 90 | 30 |
| 8 | 125 | 0 | 0 | 0 | 0 | 90 | 10* 90 at 62.5 ppm; 100 at 250 ppm | 100 | 90 |
| 9 | 125 | 0 | 0 | 0 | 0 | 80 | 70 | 100 | 80 |
| 10 | 125 | 0 | 0 | 0 | 0 | 100 | 100 | 100 | 100 |
| 10-R | 125 | 0 | 0 | 0 | 0 | 95 | 100 | 100 | 95 |
| 10-S | 125 | 0 | 0 | 0 | 0 | 95 | 100 | 100 | 95 |
| 11 | 125 | 40* 0 at 62.5 ppm | 0 | 0 | 85* 0 at 62.5 ppm | 85 | 100 | 100 | 85 |
| 12 | 125 | 0 | 0 | 0 | 0 | 40 | 85 | 95 | 90 |
| 13 | 125 | 0 | 0 | 0 | 0 | 90 | 100 | 100 | 95 |
| 14 | 125 | 0 | 0 | 0 | 0 | 75 | 100 | 100 | 100 |
| 15 | 125 | 0 | 0 | 0 | 0 | 100 | 100 | 10* 100 at 62.5; 100 at 250 | 100 |
| 16 | 125 | 0 | 0 | 0 | 0 | 100 | 100 | 100 | 90 |
| 17 | 125 | 0 | 0 | 0 | 0 | 100 | 100 | 95 | 90 |
| 18 | 125 | 0 | 0 | 0 | 0 | 100 | 100 | 100 | 100 |
| 19 | 125 | 0 | 0 | 0 | 0 | 100 | 100 | 100 | 100 |
| 20 | 125 | 0 | 0 | 0 | 0 | 100 | 100 | 100 | 100 |
| 21 | 125 | 0 | 0 | 0 | 0 | 100 | 100 | 100 | 100 |
| 22 | 125 | 0 | 0 | 0 | 0 | 100 | 100 | 100 | 90 |
| 23 | 125 | 0 | 0 | 0 | 0 | 100 | 100 | 100 | 80 |
| 24 | 125 | 0 | 0 | 0 | 0 | 100 | 100 | 100 | 90 |

TABLE XIII-continued

| Compound Tested | Dosage in PPM | Percent Kill and Control of Plant Species | | | | | | | |
|---|---|---|---|---|---|---|---|---|---|
| | | Cotton | Rape | Soybean | Sugarbeet | Giant Foxtail | Johnson Grass | Barnyard Grass | Wild Oat |
| 25 | 125 | 0 | 20* 0 at 62.5 | 0 | 0 | 100 | 100 | 100 | 90 |
| 26 | 100 | 0 | 0 | 0 | 0 | 100 | 95 | 100 | 100 |
| 27 | 125 | 0 | 0 | 0 | 0 | 98 | 100 | 100 | 80 |
| 28 | 32.9 | 0 | 60 | 0 | 0 | 90 | 90 | 100 | 90 |
| 29 | 125 | 0 | 0 | 0 | 0 | 88 | 100 | 100 | 100 |
| 30 | 125 | 0 | 50 | 0 | 50 | 90 | 85 | 100 | 85 |
| 31 | 125 | 0 | 0 | 0 | 0 | 95 | 100 | 100 | 95 |
| 32 | 125 | 0 | 0 | 0 | 0 | 95 | 100 | 100 | 95 |

Compound 10 = racemic mixture; Compound 10-R = R optical isomer; Compound 10-S = S optical isomer

EXAMPLE XVI

Postemergent Evaluation

In representative operations, each compound to be utilized in a series of tests is dissolved in acetone to one-third of the final volume to be used and the acetone solution in each case is brought up to the full volume with a solution composed of 98.0 percent water and 2.0 percent Dash TM (a spray tank adjuvant which is a mixture of petroleum hydrocarbons, alkyl esters and acids, anionic surfactants and inert materials, a proprietary material of BASF Corp., Parsippany, N.J.). The compositions, generally in the nature of an emulsion, were sprayed using a tracksprayer at a carrier volume equal to 20 gallons per acre, using an 8002 nozzle traveling at 2 mph and 40 psi, on separate respective plant species which had been grown in a greenhouse to a height of 2-6 inches in soil of good nutrient content. Sufficient amounts were employed to provide various application rates as listed in the table. The various beds were positioned side by side and exposed to substantially identical conditions of temperature and light. Each bed was maintained so as to prevent any interaction with test compounds in different plant beds. Other plant beds were treated with a acetone/water/Dash TM mixture containing no test compound to serve as controls. After treatment, the plants were maintained for about 2 weeks under greenhouse conditions conducive for good plant growth and watered as necessary. The specific plant species, test compound and dosage and the percent postemergent control obtained are set forth in Table XIV. Control refers to the reduction in growth compared to the observed results of the same untreated species.

TABLE XIV

| Compd. Tested | Dosage in g/ha | Percent Kill and Control of Plant Species | | | | | | | | |
|---|---|---|---|---|---|---|---|---|---|---|
| | | Corn | Barnyard Grass | Crabgrass | Fall Panicum | Green Foxtail | Giant Foxtail | Yellow Foxtail | Signal Grass | Sorghum |
| 10 | 2.19 | 0 | 90 | 30 | 100 | 55 | 55 | 65 | 75 | 80 |
| | 4.38 | 0 | 90 | 50 | 95 | 60 | 50 | 75 | 70 | 90 |
| | 8.75 | 10 | 90 | 60 | 95 | 95 | 90 | 95 | 85 | 90 |
| | 17.50 | 10 | 95 | 85 | 95 | 100 | 95 | 95 | 100 | 95 |
| 10-R | 2.19 | 15 | 35 | 0 | NT | 40 | 15 | 10 | 35 | 80 |
| | 4.38 | 15 | 80 | 40 | NT | 80 | 70 | 25 | 85 | 90 |
| | 8.75 | 15 | 90 | 50 | NT | 90 | 85 | 65 | 80 | 95 |
| 10-S | 2.19 | 5 | 85 | 35 | NT | 80 | 25 | 35 | 30 | 70 |
| | 4.38 | 15 | 90 | 80 | NT | 90 | 75 | 40 | 50 | 95 |
| 25 | 2.19 | 0 | 70 | 10 | 30 | 25 | 35 | 15 | 15 | 15 |
| | 4.38 | 0 | 95 | 15 | 85 | 40 | 65 | 50 | 65 | 60 |
| | 8.75 | 0 | 95 | 30 | 90 | 50 | 70 | 90 | 65 | 80 |
| | 17.50 | 0 | 95 | 60 | 95 | 95 | 90 | 90 | 90 | 95 |
| | 35.00 | 10 | 100 | 70 | 90 | 95 | 90 | 100 | 95 | 90 |
| 28 | 3.91 | 10 | 100 | 0 | 80 | 20 | 60 | 0 | 75 | 0 |
| | 7.81 | 10 | 100 | 0 | 70 | 45 | 80 | 0 | 70 | 10 |
| | 15.63 | 10 | 100 | 0 | 90 | 70 | 85 | 40 | 60 | 20 |
| | 31.25 | 15 | 100 | 0 | 90 | 80 | 90 | 45 | 85 | 70 |
| 29 | 4.38 | 10 | 75 | 35 | 85 | 50 | 20 | 83 | 95 | 85 |
| | 8.75 | 15 | 95 | 60 | 100 | 80 | 40 | 95 | 95 | 95 |
| 30 | 4.38 | 10 | 90 | 10 | 90 | 35 | 55 | 75 | 95 | 30 |
| 38 | 4.38 | 0 | 85 | 10 | 80 | 35 | 30 | 85 | 85 | 60 |
| | 8.75 | 10 | 95 | 20 | 85 | 55 | 40 | 85 | 90 | 75 |
| | 17.50 | 10 | 95 | 40 | 90 | 70 | 50 | 95 | 95 | 85 |
| | 35.00 | 15 | 95 | 60 | 95 | 90 | 95 | 95 | 95 | 90 |
| 39 | 4.38 | 0 | 95 | 10 | 85 | 50 | 15 | 80 | 65 | 20 |
| | 8.75 | 0 | 98 | 10 | 95 | 70 | 55 | 95 | 75 | 20 |
| | 17.50 | 10 | 98 | 20 | 95 | 70 | 65 | 100 | 100 | 45 |
| | 35.00 | 10 | 100 | 20 | 100 | 75 | 75 | 100 | 90 | 55 |
| 40 | 4.38 | 0 | 60 | 30 | 65 | 65 | 85 | 55 | 65 | 60 |
| | 8.75 | 5 | 90 | 45 | 70 | 70 | 90 | 65 | 70 | 95 |
| | 17.50 | 15 | 95 | 65 | 90 | 100 | 85 | 65 | 75 | 98 | g/ha = grams of active material per hectare; NT = not tested; Compound 10-R = R optical isomer; Compound 10-S = S optical isomer

EXAMPLE XVII

Pre-Emergent Evaluation

In representative operations, each compound to be utilized in a series of tests is dissolved in acetone to one-half of the final volume (twice the final concentration) to be used and the acetone solution in each case is admixed with an equal volume of water containing 0.1 percent by weight of a nonionic surfactant TWEEN ® 20 (a polyoxyethylene sorbitan monolaurate). The compositions, generally in the nature of an emulsion, were employed to spray seed beds of separate respective plant species which had been planted in soil of good nutrient content in a greenhouse. Sufficient amounts were employed to provide various application rates as listed in the table. The various beds were positioned side by side and exposed to substantially identical conditions of temperature and light. Each bed was maintained so as to prevent any interaction with test compounds in different seed beds. Other seed beds were treated with an acetone/TWEEN ® 20/water mixture containing no test compound to serve as controls. After treatment, the seed beds were maintained for about three weeks under greenhouse conditions conducive for good plant growth and watered as necessary. The specific plant species, test compound and dosage and the percent postemergent control obtained are set forth in Table XV. Control refers to the reduction in growth compared to the observed results of the same untreated species.

TABLE XV

| Compound Tested | Dosage in Kg/ha | Cotton | Rape | Soybean | Sugarbeet | Sunflower | Giant Foxtail | Johnson Grass | Barnyard Grass | Wild Oat |
|---|---|---|---|---|---|---|---|---|---|---|
| 1 | 0.28 | 10* 0 at 0.14 | 0 | 35* 0 at 0.14 | 0 | 10* 0 at 0.14 | 70 | 80 | 60 | 70 |
| 2 | 0.28 | 20 | NT | 20* 0 at 0.14 | 0 | 10* 0 at 0.14 | 80 | 40 | 95 | 50 |
| 3 | 0.56 | 0 | 0 | 0 | 0 | 20* 0 at 0.14 | 100 | 99 | 100 | 60 |
| 4 | 0.28 | 0 | 0 | 0 | 0 | 0 | 60* 100 at 0.56 | 50 | 100 | 0* 50 at 0.56 |
| 5 | 0.28 | 20* 0 at 0.14 | 20* 0 at 0.14 | 0 | 0 | 25* 0 at 0.14 | 100 | 100 | 100 | 80 |
| 6 | 0.28 | 10 | 0 | 30 | 0 | 20 | 40 | 80 | 100 | 80 |
| 7 | 1.12 | 20* 0 at 0.56 | 10 | 0 | - | 0 | 80 | 70 | 100 | 70 |
| 8 | 0.56 | 0 | NT | 40* 0 at 0.28 | 0 | 20* 0 at 0.28 | 100 | 20 | 100 | 70 |
| 9 | 0.56 | 0 | 0 | 0 | 0 | 0 | 50 | 50 | 100 | 50 |
| 10 | 0.28 | 0 | 0 | 0 | 0 | 30* 0 at 0.14 | 100 | 80 | 100 | 30 |
| 11 | 0.56 | 0 | 0 | 0 | 0 | 0 | 100 | 70 | 100 | 20 |
| 12 | 1.12 | 0 | 0 | 20 | 0 | 0 | 100 | 40 | 100 | 85 |
| 13 | 0.28 | 0 | 0 | 0 | 0 | 0 | 1000 | 95 | 100 | 100 |
| 14 | 0.56 | 0 | 0 | 0 | 0 | 0 | 100 | 90 | 100 | 100 |
| 15 | 0.56 | 0 | 0 | 0 | 30 | 20 | 98 | 75 | 100 | 80 |
| 16 | 2.24 | 0 | 0 | 0 | 0 | 0 | 100 | 95 | 100 | 100 |
| 17 | 0.28 | 30 | 0 | 30 | 0 | 20 | 20 | 100 | 50 | 50 |
| 18 | 0.28 | 0 | 0 | 30 | 0 | 30 | 0* 20 at 0.14 | 50 | 100 | 430 |
| 19 | 0.28 | 20* 0 at 0.07 | 0 | 20* 0 at 0.14 | 0 | 0* 0 at 0.14 | 30 | 30 | 100 | 20 |
| 20 | 0.28 | 0 | 0 | 40* 0 at 0.07 | 30* 0 at 0.14 | 10* 0 at 0.14 | 100 | 50 | 100 | 100 |
| 21 | 0.28 | 20* 0 at 0.14 | 0 | NT | NT | 20* 0 at 0.14 | 90 | 40 | 100 | 30 |
| 22 | 0.56 | 30* 0 at 0.28 | 10* 0 at 0.28 | 30* 0 at 0.28 | 20* 0 at 0.28 | 0 | 100 | 70 | 100 | 20 |
| 23 | 0.28 | 0 | 0 | 0 | 0 | 0 | 100 | 70 | 100 | 60 |
| 24 | 0.28 | 0 | 0 | 0 | NT | 0 | 100 | 30 | 100 | 60 |
| 25 | 1.12 | 0 | 0 | 0 | 0 | 0 | 100 | 95 | 100 | 100 |
| 26 | 0.56 | 10* 0 at 0.28 | 0 | 0 | 0 | 35 | 100 | 100 | 100 | 90 |
| 27 | 1.12 | 0 | 0 | 0 | 0 | 0 | 100 | 100 | 100 | 100 |
| 29 | 0.28 | 85* 0 at 0.025 | 0 | 10* 0 at 0.025 | 20* 0 at 0.14 | 0 | 40 | 80 | 100 | 80 |
| 30 | 0.28 | 0 | 10 | 0 | 0 | 0 | 0 | 100 | 100 | 85 |
| 31 | 0.56 | 0 | 0 | 10* 0 at 0.28 | 0 | 0 | 0 | 100 | 100 | 100 |
| 32 | 0.56 | 20* 0 at 0.28 | 0 | 0 | 0 | 20* 0 at 0.28 | 100 | 100 | 100 | 98 |
| 33 | 0.28 | 0 | 0 | 0 | 0 | 0 | 90 | 60 | 100 | 75 |
| 37 | 0.28 | 0 | 0 | 20 | 0 | 25 | 50 | 80 | 100 | 50 |
| 39 | 0.56 | 0 | 0 | 0 | 0 | 20 | 50 | 50 | 100 | 80 |

Other compounds, not specifically exemplified, but within the scope of the present invention may also be employed in the same manner as set forth hereinabove to control grassy weeds, including non-listed grassy weeds growing in both broad-leafed and grassy crops with results commensurate to those described hereinabove.

Various modifications may be made in the present invention without departing from the spirit or scope thereof and it is understood that we limit ourselves only as defined in the appended claims.

What is claimed is:

1. A substituted cyclohexanedione compound corresponding to the formula

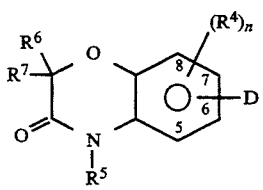

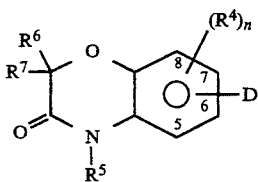

Wherein

D is attached in the 6 or 7 ring position and represents the radical

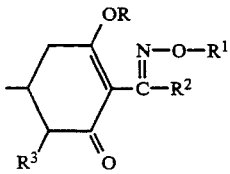

R represents —H or acyl;

R$^1$ represents $C_1$–$C_3$ alkyl, $C_3$–$C_5$ alkenyl, $C_3$–$C_5$ haloalkenyl, arylalkenyl wherein aryl represents phenyl or pyridinyl substituted with from 0 to 4 halo or —$CF_3$ groups or mixtures thereof and alkenyl contains from $C_2$–$C_5$ carbon atoms;

R$^2$ represents $C_1$–$C_3$ alkyl;

R$^3$ represents —H or —$CH_3$;

R$^4$ each independently represents —H, halo, $C_1$–$C_4$ alkyl or $C_1$–$C_4$ alkoxy;

R$^5$ represents —H, $C_1$–$C_4$ alkyl, $C_1$–$C_4$ haloalkyl, $C_3$–$C_5$ alkenyl, $C_3$–$C_5$ haloalkenyl, $C_3$–$C_5$alkynyl, $C_3$–$C_5$ haloalkynyl, alkoxyalkyl wherein the alkoxy and alkyl group each contains from $C_1$–$C_4$ carbon atoms or alkylthioalkyl wherein each alkyl group thereof contains from $C_1$–$C_4$ carbon atoms;

R$^6$ represents R$^5$, $C_1$–$C_4$ alkoxy or aryl wherein aryl is phenyl or pyridinyl substituted with from 0–3 halogen or methyl groups;

R$^7$ represents —H or $C_1$–$C_4$ alkyl; and n represents the integer 1, 2 or 3 and the herbicidally acceptable organic and inorganic salts thereof.

2. A compound as defined in Claim 1 wherein R is hydrogen.

3. The compound as defined in Claim 2 which is 2-(1-(Ethoxyimino)propyl)-3-hydroxy-5-(3-oxo-(2H, 4H)-1,4-benzoxazin-6-yl)cyclohex-2-en-1-one.

4. The compound as defined in Claim 2 which is 2-(1-(Ethoxyimino)propyl)-3-hydroxy-5-(N-methyl-3-oxo-(2H)-1,4-benzoxazin-6-yl)cyclohex-2-en-1-one.

5. The compound as defined in Claim 2 which is 2-(1-(Ethoxyimino)propyl)-3-hydroxy-5-(3-oxo-(2H, 4H)-1,4-benzoxazin-7-yl )cyclohex-2-en-1-one.

6. The compound as defined in Claim 2 which is 2-(1-(2-Ethoxyimino)propyl)-3-hydroxy-5-(2-methyl-3-oxo-(2H, 4H)-1,4-benzoxazin-6-yl )cyclohex-2-en-1-one.

7. The compound as defined in Claim 2 which is 2-(1-(2-Ethoxyimino)propyl)-3-hydroxy-5-(2,2-dimethyl-3-oxo-(2H, 4H)-1,4-benzoxazin-6-yl)cyclohex-2-en-1-one.

8. The compound as defined in Claim 2 which is 2-(1-(2-Ethoxyimino)propyl)-3-hydroxy-5-(2-phenyl-3-oxo-(2H, 4H)-1,4-benzoxazin-6-yl)cyclohex-2-en-1-one.

9. A herbicidal composition which comprises an inert carrier in intimate admixture with a herbicidally effective amount of an active ingredient which is a substituted cyclohexanedione compound corresponding to the formula

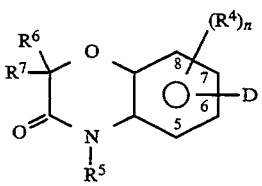

Wherein

D is attached in the 6 or 7 ring position and represents the radical

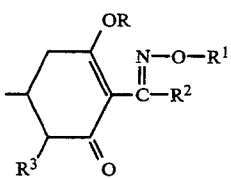

R represents —H, acyl or an alkali metal cation;

R$^1$ represents $C_1$–$C_3$ alkyl, $C_3$–$C_5$ alkenyl, $C_3$–$C_5$ haloalkenyl, arylalkenyl wherein aryl represents phenyl or pyridinyl substituted with from 0 to 4 halo or —$CF_3$ groups or mixtures thereof and alkenyl contains from $C_2$—$C_5$ carbon atoms;

R$^2$ represents $C_1$–$C_3$ alkyl;

R$^3$ represents —H or —$CH_3$;

R$^4$ each independently represents —H, halo, $C_1$–$C_4$ alkyl or $C_1$–$C_4$ alkoxy;

R$^5$ represents —H, $C_1$–$C_4$ alkyl, $C_1$–$C_4$ haloalkyl, $C_3$–$C_5$ alkenyl, $C_3$–$C_5$ haloalkenyl, $C_3$–$C_5$alkynyl, $C_3$–$C_5$ haloalkynyl, alkoxyalkyl wherein the alkoxy and alkyl group each contains from $C_1$–$C_4$ carbon atoms or alkylthioalkyl wherein each alkyl group thereof contains from $C_1$–$C_4$ carbon atoms;

R$^6$ represents R$^5$, $C_1$–$C_4$ alkoxy or aryl wherein aryl is phenyl or pyridinyl substituted with from 0–3 halogen or methyl groups.

R$^7$ represents —H or $C_1$–$C_4$ alkyl; and n represents the integer 1, 2 or 3 and the herbicidally acceptable organic and inorganic salts thereof.

10. A composition as defined in Claim 8 wherein R is hydrogen.

11. The composition as defined in Claim 10 wherein the active ingredient is 2-(1-(Ethoxyimino)-propyl)-3-hydroxy-5-(3-oxo-(2H, 4H)-1,4-benzoxazin-6-yl)cyclohex-2-en-1-one.

12. The composition as defined in Claim 10 wherein the active ingredient is 2-(1-(Ethoxyimino)-propyl)-3-hydroxy-5-(N-methyl-3-oxo-(2H) -1,4-benzoxazin-6-yl)cyclohex-2-en-1-one.

13. The composition as defined in Claim 10 wherein the active ingredient is 2-(1-(Ethoxyimino)-propyl)-3-hydroxy-5-(3-oxo-(2H, 4H)-1,4-benzoxazin-7-yl) cyclohex-2-en-1-one.

14. The composition as defined in Claim 10 wherein the active ingredient is 2-(1-(2-Ethoxyimino)propyl)-3-hydroxy-5-(2-methyl-3-oxo-(2H, 4H )-1,4-benzoxazin-6-yl)cyclohex-2-en-1-one.

15. The composition as defined in Claim 10 wherein the active ingredient is 2-(1-(2-Ethoxyimino)-propyl)-3-hydroxy-5-(2,2-dimethyl-3-oxo-(2H, 4H)-1,4-benzoxazin-6-yl) cyclohex-2-en-1-one.

16. The composition as defined in Claim 10 wherein the active ingredient is 2-(1-(2-Ethoxyimino)-propyl)-3-hydroxy-5-(2-phenyl-3-oxo-(2H, 4H)-1,4-benzoxazin-6-yl)cyclohex-2-en-1-one.

17. A method for the kill or control of grassy weeds which comprises contacting said weeds or their habitat with a herbicidally effective amount of a composition which comprises an inert carrier in intimate admixture with a herbicidally active ingredient which is a substituted cyclohexanedione compound corresponding to the formula

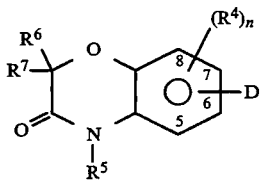

I

Wherein
D is attached in the 6 or 7 ring position and represents the radical

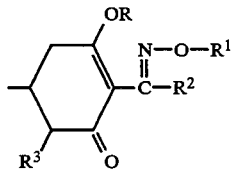

R represents —H, acyl or an alkali metal cation;
$R^1$ represents $C_1-C_3$ alkyl, $C_3-C_5$ alkenyl, $C_3-C_5$ haloalkenyl, arylalkenyl wherein aryl represents phenyl or pyridinyl substituted with from 0 to 4 halo or —$CF_3$ groups or mixtures thereof and alkenyl contains from $C_3-C_5$ carbon atoms;
$R^2$ represents $C_1-C_3$ alkyl;
$R^3$ represents —H or —$CH_3$;
$R^4$ each independently represents —H, halo, $C_1-C_4$ alkyl or $C_1-C_4$ alkoxy;
$R^5$ represents —H, $C_1-C_4$ alkyl, $C_1-C_4$ haloalkyl, $C_3-C_5$ alkenyl, $C_3-C_5$ haloalkenyl, $C_3-C_5$ alkynyl, $C_3-C_5$ haloalkynyl, alkoxyalkyl wherein the alkoxy and alkyl group each contains from $C_1-C_4$ carbon atoms or alkylthioalkyl wherein each alkyl group thereof contains from $C_1-C_4$ carbon atoms;
$R^6$ represents $R^5$, $C_1-C_4$ alkoxy or aryl wherein aryl is phenyl or pyridinyl substituted with from 0-3 halogen or methyl groups.
$R^7$ represents —H or $C_1-C_4$ alkyl; and
n represents the integer 1, 2 or 3
and the herbicidally acceptable organic and inorganic salts thereof.

18. A method as defined in Claim 17 wherein R is hydrogen.

19. The method as defined in Claim 18 wherein the active ingredient is 2-(1-(Ethoxyimino)propyl)-3-hydroxy- 5-(3-oxo-(2H, 4H)-1,4-benzoxazin-6-yl)cyclohex-2-en-1-one.

20. The method as defined in Claim 18 wherein the active ingredient is 2-(1-(Ethoxyimino)propyl)-3-hydroxy-5-(N-methyl-3-oxo-(2H)-1,4-benzoxazin-6-yl)cyclohex-2-en-1-one.

21. The method as defined in Claim 18 wherein the active ingredient is 2-(1-(Ethoxyimino)propyl)-3-hydroxy-5-(3-oxo-(2H, 4H)-1,4-benzoxazin-7-yl)cyclohex-2-en-1-one.

22. The method as defined in Claim 18 wherein the active ingredient is 2-(1-(2-Ethoxyimino)propyl)-3-hydroxy-5-(2-methyl-3-oxo-(2H, 4H)-1,4-benzoxazin-6-yl)cyclohex-2-en-1-one.

23. The method as defined in Claim 18 wherein the active ingredient is 2-(1-(2-Ethoxyimino)propyl)-3-hydroxy-5-(2,2-dimethyl-3-oxo-(2H, 4H)-1,4-benzoxazin-6-yl) cyclohex-2-en-1-one.

24. The method as defined in Claim 18 wherein the active ingredient is 2-(1-(2-Ethoxyimino)propyl)-3-hydroxy-5-(2-phenyl-3-oxo-(2H, 4H)-1,4-benzoxazin-6-yl)cyclohex-2-en-1-one.

* * * * *